US006297366B1

(12) United States Patent
Gudkov et al.

(10) Patent No.: US 6,297,366 B1
(45) Date of Patent: Oct. 2, 2001

(54) ING-ENCODED P33$^{ING1}$ PROTEIN AS A MEDIATOR OF P53 SIGNALING PATHWAY IN MAMMALIAN CELLS

(75) Inventors: Andrei Gudkov, Glencoe, IL (US); Igor Garkavstev, Cambridge, MA (US); Karl Riabowol, Calgary (CA)

(73) Assignee: Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 09/006,783

(22) Filed: Jan. 14, 1998

(51) Int. Cl.$^7$ .................................................. C07H 21/04
(52) U.S. Cl. ...................... 536/23.5; 536/23.1; 536/24.1; 435/325
(58) Field of Search ................................ 536/23.1, 23.5, 536/24.1; 435/325

(56) References Cited

U.S. PATENT DOCUMENTS 5,217,889    6/1993   Roninson et al. .

FOREIGN PATENT DOCUMENTS

WO97/21809    6/1997   (WO) .

OTHER PUBLICATIONS

Ossovskaya et al., 1996, Proc. Natl. Acad. Sci. USA 93: 10309–10314.
Sambrook et al., 1990, Molecular Cloning: A Laboratory Manual (Cold Springs Harbor Press: New York) Table of Contents.
Uhlamann and Peyman,1990, Chemical Reviews 90: 543–584.
Kawasaki & Wang, 1989, in PCR Technology, (Erlich, ed.) Stockton Press: New York, pp. 89–98.
Lowe et al., 1993, Cell 74: 957–967.
Kopnin et al., 1995, Oncol. Res. 7: 299–306.
El–Deiry et al., 1993, Cell 75: 817–825.
Kondratov et al., 1996, Molecular Biology (Russia) :613–620.
Harlow & Lane, 1988, Antibodies: A Laboratory Manual, Cold Spring Harbor Laboratory Press: New York, p. 447.
Agarwal et al., 1995, Proc. Natl. Acad. Sci. USA 92: 8493–8497.
Momand et al., 1992, Cell 69: 1237–1245.
Jayaraman et al., 1997, Genes Devel. 11: 558–570.
Avantaggiati et al., 1997, Cell 89: 1175–1184.
Chen et al. Cell 47:381–389 (1986).*
Holzmayer et al. Nucleic Acids Res 20: 711–717 (1992).*
Gudkov et al. Proc. Natl. Acad Sci. 90: 3231–3235 (1993).
Schneider & Banner, Tetrahedron Letters 31:335 (1990).
Culver et al. Science 256:1550–1552 (1992).
Miller & Rosman, Biotechnologies 7:980–986 (1989).
Bodine et al Proc Natl Acad Sci USA 87:3738–3742 (1990).
Baim et al. Proc Natl Acad Sci USA 88:5072–5076 (1991).
Lau and Nathans, EMBO J. 4:3145–3151 (1985).
Lau and Nathans, Proc. Natl Acad Sci USA 84:1182–1186 (1987).
Noonan et al Proc Natl Acad Sci USA 87:7160–7164 (1990).
Markowitz et al., Virology 167: 400–406 (1988).
Patanjali et al., Proc. Natl. Acad. Sci. USA 88:1943–1947(1991).
Ohara et al., Proc. Natl. Acad. Sci. USA 86:5673–5677 (1989).
Kinzler et al., 1987, Science 236: 70–73.
Schwab et al., 1989, Oncogene 4:139–144.
Nakatani et al., Jpn. J. Cancer Res. 81: 707–710, 1990.
Hunter, 1991, Cell 64: 249–270.
Weinberg 1991, Science 254:1138–1146.
Fearon et al., 1990, Science 247: 49–56.
Sap et al., 1986, Nature 324: 635–640.
Weinberger et al., 1986, Nature 324: 641–646.
Xu et al., 1990, Cell 62: 599–608.
Ballester et al., 1990, Cell 62: 851–859.
Buchberg et al., 1990, Nature 347:291–294.
Barbacid, 1987, Ann. Rev. Biochem. 56: 779–827.
Fields et al., 1990 Science, 249:1046–1049.
Raycroft et al., 1990, Science 249: 1049–1051.
Kern et al., 1991, Oncogene 6: 131–136.
O'Rourke et al., 1990, Oncogene 5:1829–1832.
Kern et al., 1991, Science 252: 1708–1711.
Lee et al., 1987, Nature 329: 642–645.
Friend et al., 1987, Proc. Natl. Acad. Sci. USA 84:9059–9063.
Call et al., 1990, Cell 60: 509–520.
Gessler et al., 1990, Nature 343: 774–778.
Friend et al., 1991, Science 251:1366–1370.
Viskochil et al., 1990, Cell 62: 187–192.
Vogelstein et al., 1988, N. Engl. J. Med. 319:525–532.
Solomon et al., 1991, Science, 254: 1153–1160.
Laforgia et al., 1991, Proc. Natl. Acad. Sci. USA 88: 5036–5040.
Trent et al., 1989, Cancer Res. 49: 420–423.
Milner et al., 1991, Molec. Cell. Biol. 11: 12–19.
Eliyahu et al., 1984, Nature 312: 646–659.
Parada et al., 1984, Nature 312: 649–651.
Graf & Beug, 1983, Cell 34: 7–9.
Damm et al., 1989, Nature 339: 593–597.
Montenarh & Quasier, 1989, Oncogene 4: 379–382.
Finlay et al., 1988, Molec. Cell Biol. 8: 531–539.

(List continued on next page.)

*Primary Examiner*—Sheela Huff
*Assistant Examiner*—Larry R. Helms
(74) *Attorney, Agent, or Firm*—McDonnell Boehnen Hulbert & Berghoff

(57) ABSTRACT

The invention relates to a novel tumor suppressor gene, termed ING, genetic suppressor elements derived from this gene, and the protein produced by expression of this gene, known as p33$^{ING1}$. The invention provides methods for characterizing mammalian cells on the basis of whether such cells express the ING gene, and embodiments of such methods directed at malignant or pre-malignant tissues in an animal for assaying the risk of developing malignant disease by the animal.

3 Claims, 11 Drawing Sheets

OTHER PUBLICATIONS

Damm et al., 1987, EMBO J. 6: 375–382.
Sap et al., 1989, Nature, 340:242–244.
Gudkov et al., 1993, Proc. Natl. Acad. Sci. USA 90: 3231–3235.
Shih et al., 1979, Proc. Natl. Acad. Sci. USA 76:5714–5718.
Pauwels et al., 1988, J. Virol. Meth. 20: 309–321.
Wolos et al., 1993, J. Immunol, 150:3264–3273.
Liu et al., 1992, Antivir. Res. 19: 247–265.
Duerre et al., 1992, Biochem. Biolog. Cell. 70:703–711.
Perlaky et al., 1992, Cancer Res. 52: 428–436.
Vale, 1987, Ann. Rev. Cell Biol. 3:347–378.
Bender et al., 1987, J. Virol 61: 1639–1646.
Varmus, 1989, Weinberg, Cold Springs Harbor Press, Cold Spring Harbor, N.Y. pp. 3–44.
Albritton et al., 1989, Cell 57:659–666.
McConkey et al., 1989, Arch. Biochem. Biophys. 269:365–370.
Altshul et al., 1990, J. Mol. Biol. 215:403–410.
Kung et al., 1990, Cancer Res. 50:7307–7317.
Herskowitz, 1987, Nature 329: 219–222.
Garkavstev et al., 1996, Nature Genetics 14: 415–420.
Garkavstev et al., 1997, Mol. Cell Biol. 17:2014–2019.
Helbing et al., 1997, Cancer Res. 57:1255–1258.
Gottlieb & Oren, 1996, Biochem. Biophys. Acta Rev. Cancer 1287: 77–102.
Garkavstev et al., 1997, Cytogenet. Cell Genet. 76: 176–178.
Zeremski et al., 1997, Somatic Cell Mol. Genet. 23: 233–236.
Maestro et al., 1996, Cancer Res. 56: 1146–1150.

* cited by examiner

FIGURE 1

```
TTGTAGTTTC TAAAATGCTG ATCCACAGAC CACTTTCTTG TTACACGTGT ACCAATGAAA        60

ACAAAAGGCA AACAGAATCA CTGCCATCCC TATGAAAGGA ATGGTTCCTT TTCTAACATT       120

CTTTAAAAAT ATACATTTTA CACTCCTTGC ACCTCAACAA AGGCAGCAAT GTAATAAATA       180

```
GAGTAACCCG ATAAT ATG CCG TTG TGC ACG GCG ACG AGA ATT CCC AGA TAT              51
                Met Pro Leu Cys Thr Ala Thr Arg Ile Pro Arg Tyr
                 1                5                       10

AGC AGT AGC AGT GAT CCC GGG CCT GTG GCT CGG GCC GGG GGC TGC AGT              99
Ser Ser Ser Ser Asp Pro Gly Pro Val Ala Arg Gly Arg Gly Cys Ser
            15                  20                  25

TCG GAC CGC CTC CCG CGA CCC GCG GGG CCG GCT CGG AGA CAG TTT CAG             147
Ser Asp Arg Leu Pro Arg Pro Ala Gly Pro Ala Arg Arg Gln Phe Gln
         30                  35                  40

GCC GCA TCT TTG CTG ACC CGA GGG TGG GGC CGC GCG TGG CCG TGG AAA             195
Ala Ala Ser Leu Leu Thr Arg Gly Trp Gly Arg Ala Trp Pro Trp Lys
 45                  50                  55                  60

CAG ATC CTG AAG GCG CTA GAC GAG TGC TAC GAG CGC TTC AGT CGC GAG             243
Gln Ile Leu Lys Ala Leu Asp Glu Cys Tyr Glu Arg Phe Ser Arg Glu
                 65                  70                  75

ACA GAC GGG GCG CAG AAG CGG CGG ATG CTG CAC TGT GTG CAG CGC GCG             291
Thr Asp Gly Ala Gln Lys Arg Arg Met Leu His Cys Val Gln Arg Ala
             80                  85                  90

CTG ATC CGC AGC CAG GAG CTG GGC GAC GAG AAG ATC CAG ATC GTG AGC             339
Leu Ile Arg Ser Gln Glu Leu Gly Asp Glu Lys Ile Gln Ile Val Ser
         95                 100                 105

CAG ATG GTG GAG CTG GTG GAG AAC CGC ACG CGG CAG GTG GAC AGC CAC             387
Gln Met Val Glu Leu Val Glu Asn Arg Thr Arg Gln Val Asp Ser His
    110                 115                 120

GTG GAG CTG TTC GAG GCG CAG CAG GAG CTG GGC GAC ACA GTG GGC AAC             435
Val Glu Leu Phe Glu Ala Gln Gln Glu Leu Gly Asp Thr Val Gly Asn
125                 130                 135                 140

AGC GGC AAG GTT GGC GCG GAC AGG CCC AAT GGC GAT GCG GTA GCG CAG             483
Ser Gly Lys Val Gly Ala Asp Arg Pro Asn Gly Asp Ala Val Ala Gln
                145                 150                 155

TCT GAC AAG CCC AAC AGC AAG CGC TCA CGG CGG CAG CGC AAC AAC GAG             531
Ser Asp Lys Pro Asn Ser Lys Arg Ser Arg Arg Gln Arg Asn Asn Glu
            160                 165                 170

AAC CGT GAG AAC GCG TCC AGC AAC CAC GAC CAC GAC GAC GGC GCC TCG             579
Asn Arg Glu Asn Ala Ser Ser Asn His Asp His Asp Asp Gly Ala Ser
        175                 180                 185
```

FIGURE 2B

```
GGC ACA CCC AAG GAG AAG AAG GCC AAG ACC TCC AAG AAG AAG AAG CGC       627
Gly Thr Pro Lys Glu Lys Lys Ala Lys Thr Ser Lys Lys Lys Lys Arg
    190             195                 200

TCC AAG GCC AAG GCG GAG CGA GAG GCG TCC CCT GCC GAC CTC CCC ATC       675
Ser Lys Ala Lys Ala Glu Arg Glu Ala Ser Pro Ala Asp Leu Pro Ile
205             210                 215                 220

GAC CCC AAC GAA CCC ACG TAC TGT CTG TGC AAC CAG GTC TCC TAT GGG       723
Asp Pro Asn Glu Pro Thr Tyr Cys Leu Cys Asn Gln Val Ser Tyr Gly
                225                 230                 235

GAG ATG ATC GGC TGC GAC AAC GAC GAG TGC CCC ATC GAG TGG TTC CAC       771
Glu Met Ile Gly Cys Asp Asn Asp Glu Cys Pro Ile Glu Trp Phe His
            240                 245                 250

TTC TCG TGC GTG GGG CTC AAT CAT AAA CCC AAG GGC AAG TGG TAC TGT       819
Phe Ser Cys Val Gly Leu Asn His Lys Pro Lys Gly Lys Trp Tyr Cys
        255                 260                 265

CCC AAG TGC CGG GGG GAG AAC GAG AAG ACC ATG GAC AAA GCC CTG GAG       867
Pro Lys Cys Arg Gly Glu Asn Glu Lys Thr Met Asp Lys Ala Leu Glu
    270                 275                 280

AAA TCC AAA AAA GAG AGG GCT TAC AAC AGG TAGTTTGTGG ACAGGCGCCT         917
Lys Ser Lys Lys Glu Arg Ala Tyr Asn Arg
285             290

GGTGTGAGGA GGACAAAATA AACCGTGTAT TTATTACATT GCTGCCTTTG TTGAGGTGCA     977

AGGAGTGTAA AATGTATATT TTTAAAGAAT GTTAGAAAAG GAACCATTCC TTTCATAGGG    1037

ATGGCAGTGA TTCTGTTTGC CTTTTGTTTT CATTGGTACA CGTGTAACAA GAAAGTGGTC    1097

TGTGGATCAG CATTTTAGAA ACTACAAATA TAGGTTTGAT TCAACACTTA AGTCTCAGAC    1157

TGATTTCTTG CGGGAGGAGG GGGACTAAAC TCACCCTAAC ACATTAAATG TGGAAGGAAA    1217

ATATTTCATT AGCTTTTTTA TTTTAATACA AGTAATATTA TTACTTTATG AACAATTTTT    1277

TTTAATTGGC CATGTCGCCA AAAATACAGC CTATAGTAAA TGTGTTTCTT GCTGCCATGA    1337

TGTATATCCA TATAACAATT CAGTAACAAA GGTTTAAAGT TTGAAGATTA TTTTTTAAAA    1397

AGGTAAAAGG TTAAATTTTA CATGACAGAT ATTTTATCTA TTGGCCTGTT CCCCAAATGG    1457

CCATTTTAAA ATGCTTGGGT ACACTTCTCT TAAGTGGTCT AGTCAAGGAA CCTCAAGTCA    1517

TGCTTTTGCT ATCACCAATC ATAGTGTACC CATCTTTAAT TTATATCAGG TGTATAAATG    1577
```

FIGURE 2C

```
TACATTTCCA AATGAACTTG CACTGTAATA TTATAATTGG AAGTGCAGTC AGCAGTAGCT    1637

GTCGGAGCTA ATGTCACAAT TATGTGCAAA GGTGTGCTTC CTGCTGTATG TGAGCTGTAA    1697

AAATGTTACG TGAAGAAATA AATGAAACTT GGCCAGTTTG TTCCTCTAGT AGTATATTTA    1757

ATTTTGACAT AAGTAACTTT TAAAATTTGT CTTAAAAATT TATACACCAG CAATTTAGAC    1817

AAAGCCTTAA GCAAATTTTG TATTATTGTT CTCACTTATT ATTAATAATG AAGTAGAAGT    1877

TACTTAATTG CCAGCAAATA AATACGTGTC AAAAAAGAAT CTGTATTCAG ACCCCTGGGG    1937

TCAGGAAATT ACTGCCCCAC TTGTCAAGTT CAGCCCACCA TCTGTTTGAA CATTATATGA    1997

AGTTTAAATT CTAGTGTCCA TAAATAAAGT TTCAGCGGCA CCCCAAAAAA AAAAAAAAA    2057

AAAA                                                                 2061
``` a 10(1) CELLS TRANSDUCED WITH:
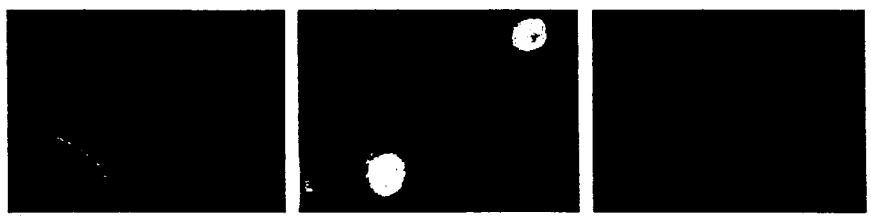
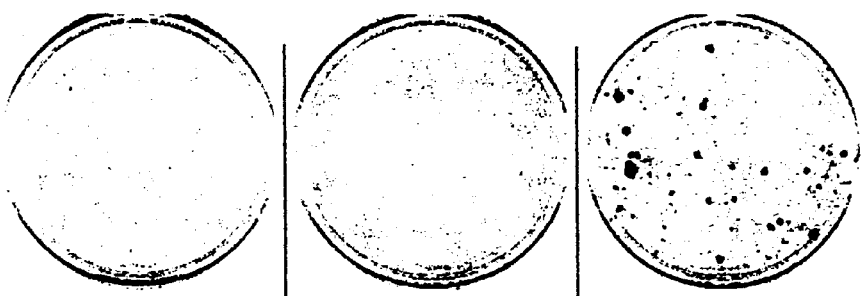
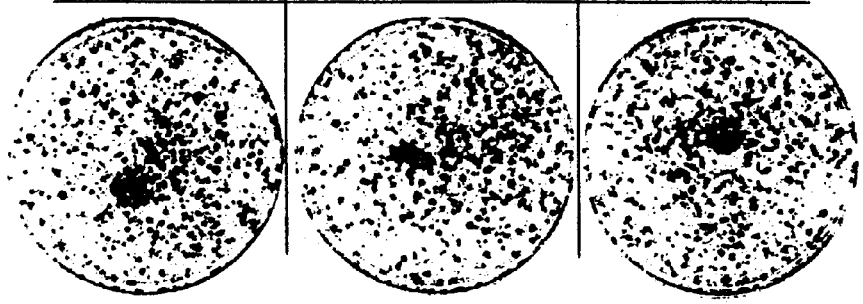
b 10(1) CELLS TRANSFECTED WITH:
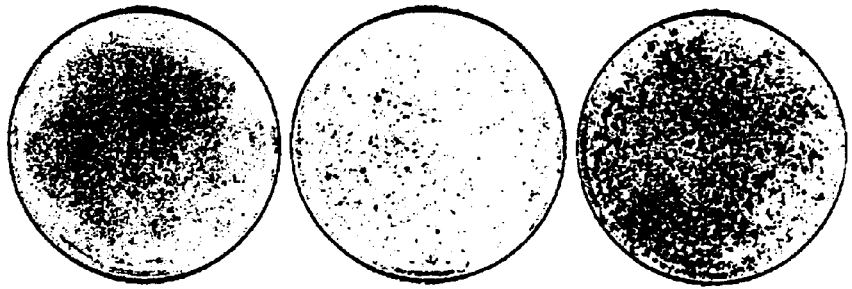
FIGURE 4

FIGURE 7A

```
TGAACC ATG TTG AGT CCT GCC AAC GGG GAG CAG CTC CAC CTG GTG AAC         48
       Met Leu Ser Pro Ala Asn Gly Glu Gln Leu His Leu Val Asn
        1           5                      10

TAT GTG GAG GAC TAC CTG GAC TCC ATC GAG TCC CTG CCT TTC GAC TTG        96
Tyr Val Glu Asp Tyr Leu Asp Ser Ile Glu Ser Leu Pro Phe Asp Leu
 15              20                  25                      30

CAG AGA AAT GTC TCG CTG ATG CGG GAG ATC GAC GCG AAA TAC CAA GAG       144
Gln Arg Asn Val Ser Leu Met Arg Glu Ile Asp Ala Lys Tyr Gln Glu
                 35                  40                  45

ATC CTG AAG GAG CTA GAC GAG TGC TAC GAG CGC TTC AGT CGC GAG ACA       192
Ile Leu Lys Glu Leu Asp Glu Cys Tyr Glu Arg Phe Ser Arg Glu Thr
             50                  55                  60

GAC GGG GCG CAG AAG CGG CGG ATG CTG CAC TGT GTG CAG CGC GCG CTG       240
Asp Gly Ala Gln Lys Arg Arg Met Leu His Cys Val Gln Arg Ala Leu
         65                  70                  75

ATC CGC AGC CAG GAG CTG GGC GAC GAG AAG ATC CAG ATC GTG AGC CAG       288
Ile Arg Ser Gln Glu Leu Gly Asp Glu Lys Ile Gln Ile Val Ser Gln
         80                  85                  90

ATG GTG GAG CTG GTG GAG AAC CGC ACG CGG CAG GTG GAC AGC CAC GTG       336
Met Val Glu Leu Val Glu Asn Arg Thr Arg Gln Val Asp Ser His Val
 95                 100                 105                 110

GAG CTG TTC GAG GCG CAG CAG GAG CTG GGC GAC ACA GTG GGC AAC AGC       384
Glu Leu Phe Glu Ala Gln Gln Glu Leu Gly Asp Thr Val Gly Asn Ser
                115                 120                 125

GGC AAG GTT GGC GCG GAC AGG CCC AAT GGC GAT GCG GTA GCG CAG TCT       432
Gly Lys Val Gly Ala Asp Arg Pro Asn Gly Asp Ala Val Ala Gln Ser
            130                 135                 140

GAC AAG CCC AAC AGC AAG CGC TCA CGG CGG CAG CGC AAC AAC GAG AAC       480
Asp Lys Pro Asn Ser Lys Arg Ser Arg Arg Gln Arg Asn Asn Glu Asn
            145                 150                 155

CGT GAG AAC GCG TCC AGC AAC CAC GAC CAC GAC GAC GGC GCC TCG GGC       528
Arg Glu Asn Ala Ser Ser Asn His Asp His Asp Asp Gly Ala Ser Gly
            160                 165                 170

ACA CCC AAG GAG AAG AAG GCC AAG ACC TCC AAG AAG AAG AAG CGC TCC       576
Thr Pro Lys Glu Lys Lys Ala Lys Thr Ser Lys Lys Lys Lys Arg Ser
175                 180                 185                 190

AAG GCC AAG GCG GAG CGA GAG GCG TCC CCT GCC GAC CTC CCC ATC GAC       624
Lys Ala Lys Ala Glu Arg Glu Ala Ser Pro Ala Asp Leu Pro Ile Asp
                195                 200                 205
```

FIGURE 7B

```
CCC AAC GAA CCC ACG TAC TGT CTG TGC AAC CAG GTC TCC TAT GGG GAG       672
Pro Asn Glu Pro Thr Tyr Cys Leu Cys Asn Gln Val Ser Tyr Gly Glu
            210                 215                 220

ATG ATC GGC TGC GAC AAC GAC GAG TGC CCC ATC GAG TGG TTC CAC TTC       720
Met Ile Gly Cys Asp Asn Asp Glu Cys Pro Ile Glu Trp Phe His Phe
            225                 230                 235

TCG TGC GTG GGG CTC AAT CAT AAA CCC AAG GGC AAG TGG TAC TGT CCC       768
Ser Cys Val Gly Leu Asn His Lys Pro Lys Gly Lys Trp Tyr Cys Pro
            240                 245                 250

AAG TGC CGG GGG GAG AAC GAG AAG ACC ATG GAC AAA GCC CTG GAG           813
Lys Cys Arg Gly Glu Asn Glu Lys Thr Met Asp Lys Ala Leu Glu
255                 260                 265

AAATCCAAAA AAGAGAGGGC TTACAACAGG TAGTTTGTGG ACAGGCGCCT GGTGTGAGGA     873
```

FIGURE 8

```
ATG CTG CAC TGT GTG CAG CGC GCG CTG ATC CGC AGC CAG GAG CTG GGC      48
Met Leu His Cys Val Gln Arg Ala Leu Ile Arg Ser Gln Glu Leu Gly
 1               5                  10                  15

GAC GAG AAG ATC CAG ATC GTG AGC CAG ATG GTG GAG CTG GTG GAG AAC      96
Asp Glu Lys Ile Gln Ile Val Ser Gln Met Val Glu Leu Val Glu Asn
                20                  25                  30

CGC ACG CGG CAG GTG GAC AGC CAC GTG GAG CTG TTC GAG GCG CAG CAG     144
Arg Thr Arg Gln Val Asp Ser His Val Glu Leu Phe Glu Ala Gln Gln
            35                  40                  45

GAG CTG GGC GAC ACA GTG GGC AAC AGC GGC AAG GTT GGC GCG GAC AGG     192
Glu Leu Gly Asp Thr Val Gly Asn Ser Gly Lys Val Gly Ala Asp Arg
        50                  55                  60

CCC AAT GGC GAT GCG GTA GCG CAG TCT GAC AAG CCC AAC AGC AAG CGC     240
Pro Asn Gly Asp Ala Val Ala Gln Ser Asp Lys Pro Asn Ser Lys Arg
 65                 70                  75                  80

TCA CGG CGG CAG CGC AAC AAC GAG AAC CGT GAG AAC GCG TCC AGC AAC     288
Ser Arg Arg Gln Arg Asn Asn Glu Asn Arg Glu Asn Ala Ser Ser Asn
                85                  90                  95

CAC GAC CAC GAC GAC GGC GCC TCG GGC ACA CCC AAG GAG AAG AAG GCC     336
His Asp His Asp Asp Gly Ala Ser Gly Thr Pro Lys Glu Lys Lys Ala
               100                 105                 110

AAG ACC TCC AAG AAG AAG AAG CGC TCC AAG GCC AAG GCG GAG CGA GAG     384
Lys Thr Ser Lys Lys Lys Lys Arg Ser Lys Ala Lys Ala Glu Arg Glu
            115                 120                 125

GCG TCC CCT GCC GAC CTC CCC ATC GAC CCC AAC GAA CCC ACG TAC TGT     432
Ala Ser Pro Ala Asp Leu Pro Ile Asp Pro Asn Glu Pro Thr Tyr Cys
        130                 135                 140

CTG TGC AAC CAG GTC TCC TAT GGG GAG ATG ATC GGC TGC GAC AAC GAC     480
Leu Cys Asn Gln Val Ser Tyr Gly Glu Met Ile Gly Cys Asp Asn Asp
145                 150                 155                 160

GAG TGC CCC ATC GAG TGG TTC CAC TTC TCG TGC GTG GGG CTC AAT CAT     528
Glu Cys Pro Ile Glu Trp Phe His Phe Ser Cys Val Gly Leu Asn His
                165                 170                 175

AAA CCC AAG GGC AAG TGG TAC TGT CCC AAG TGC CGG GGG GAG AAC GAG     576
Lys Pro Lys Gly Lys Trp Tyr Cys Pro Lys Cys Arg Gly Glu Asn Glu
            180                 185                 190

AAG ACC ATG GAC AAA GCC CTG GAG AAA TCC AAA AAA GAG AGG GCT TAC     624
Lys Thr Met Asp Lys Ala Leu Glu Lys Ser Lys Lys Glu Arg Ala Tyr
        195                 200                 205

AAC AGG TAG                                                          633
Asn Arg
    210
```

ING-ENCODED P33$^{ING1}$ PROTEIN AS A MEDIATOR OF P53 SIGNALING PATHWAY IN MAMMALIAN CELLS

This invention was made with government support under R01-CA60730 and R03-TW00475 from the National Institutes of Health. The government has certain rights in the invention.

BACKGROUND OF THE INVENTION

1. Field of the Invention

The invention relates to genetic and cellular factors associated with cellular senescence and immortalization, apoptosis, neoplastic transformation and sensitivity to chemical and physical environmental insult. More particularly, the invention also provides methods and reagents for activating a particular cellular factor, the cellular tumor suppressor known as p53, and specifically provides reagents for activating p53-dependent transcriptional activity. The reagents provided by the invention comprise recombinant expression constructs encoding all or a portion of a particular cellular gene, termed ING1, and the protein produced by expression of this gene, known as p33$^{ING1}$. The invention provides methods for using such recombinant expression constructs for activation of p53-related transcription involved in expression of apoptosis and other cellular expression pathways. The invention also provides reagents and methods for preparing genetic suppressor elements (GSEs) from ING1-encoding nucleic acid species, and methods for using such GSE for inhibiting apoptosis, delaying cellular aging, facilitating anchorage-independent growth, protecting the cell from the effects of certain cytotoxic drugs, and inhibiting the activity of p53. This invention also provides methods for characterizing mammalian cells on the basis of whether such cells express the ING1 gene, and embodiments of such methods directed at malignant or pre-malignant tissues in an animal for assaying the risk of developing malignant disease by the animal.

2. Summary of the Related Art

Cancer remains one of the leading causes of death in the United States. Clinically, a broad variety of medical approaches, including surgery, radiation therapy and chemotherapeutic drug therapy are currently being used in the treatment of human cancer (see the textbook *CANCER: Principles & Practice of Oncology*, 2d Edition, De Vita et al., eds., J. B. Lippincott Company, Philadelphia, Pa., 1985). However, it is recognized that such approaches continue to be limited by a fundamental lack of a clear understanding of the precise cellular bases of malignant transformation and neoplastic growth.

The beginnings of such an understanding of the cellular basis of malignant transformation and neoplastic growth have been elucidated over the last ten years. Growth of normal cells is now understood to be regulated by a balance of growth-promoting and growth-inhibiting genes, known as proto-oncogenes and tumor suppressor genes, respectively. Proto-oncogenes are turned into oncogenes by regulatory or structural mutations that increase their ability to stimulate uncontrolled cell growth (see Varmus, 1989, "A historical overview of oncogenes", in *Oncogenes and the Molecular Origin of Cancer*, Weinberg, ed., Cold Spring Harbor Press, Cold Spring Harbor, N.Y., pp. 3–44).

It is likely, however, that there are at least as many cancer-associated genes that are involved in suppression rather than induction of abnormal cell growth. This class of genes, known as anti-oncogenes or tumor suppressors, has been defined as comprising "genetic elements whose loss or inactivation allows a cell to display one or another phenotype of neoplastic growth deregulation" by Weinberg (1991, *Science* 254: 1138–1146). Changes in a tumor suppressor gene that result in the loss of its function or expression are recessive, because they have no phenotypic consequences in the presence of the normal allele of the same gene. The recessive nature of mutations associated with tumor suppressors makes such genes very difficult to analyze or identify by gene transfer techniques and explains why oncogene research is far more advanced than studies of tumor suppressors.

In normal cells, tumor suppressor genes may participate in growth inhibition at different levels, from the recognition of a growth inhibiting signal and its transmission to the nucleus, to the induction (or inhibition) of secondary response genes that finally determine the cellular response to the signal. The known tumor suppressor genes have indeed been associated with different steps of the regulatory pathway. Thus, the DCC and ErbA genes encode receptors of two different classes (Fearon et al., 1990, *Science* 247: 49–56; Sap et al., 1986, *Nature* 324: 635–640; Weinberger et al., 1986, *Nature* 324: 641–646). The gene NF-1 encodes a polypeptide that resembles ras-interacting proteins, that are members of the signaling pathway (Xu et al., 1990, *Cell* 62: 599–608; Ballester et al., 1990, *Cell* 62: 851–859; Buchberg et al., 1990, *Nature* 347: 291–294; Barbacid, 1987, *Ann. Rev. Biochem.* 56: 779–827). p53, RB and WT genes encode nuclear regulatory proteins (Fields et al., 1990, *Science* 249: 1046–1049; Raycroft et al., 1990, *Science* 249: 1049–1051; Kern et al., 1991, *Oncogene* 6: 131–136; O'Rourke et al., 1990, *Oncogene* 5: 1829–1832; Kern et al., 1991, *Science* 252: 1708–1711; Lee et al., 1987, *Nature* 329: 642–645; Friend et al., 1987, *Proc. Natl. Acad. Sci. USA* 84: 9059–9063; Call et al., 1990, *Cell* 60: 509–520; Gessler et al., 1990, *Nature* 343: 774–778).

Two approaches have been previously used for cloning tumor suppressor genes. The first approach is based on isolating the regions associated with nonrandom genetic deletions or rearrangements observed in certain types of tumors. This approach requires the use of extremely laborious linkage analyses and does not give any direct information concerning the function of the putative suppressor gene (Friend et al., 1991, *Science* 251: 1366–1370; Viskochil et al., 1990, *Cell* 62: 187–192; Vogelstein et al., 1988, *N. Engl. J. Med.* 319: 525–532). In fact, among numerous observations of loss of heterozygosity in certain tumors (Solomon et al., 1991, *Science* 254: 1153–1160; LaForgia et al., 1991, *Proc. Natl. Acad. Sci. USA* 88: 5036–5040; Trent et al., 1989, *Cancer Res.* 49: 420–423), there are only a few examples where the function of the affected gene is understood. In two of these rare cases the gene function was identified using another method, analysis of dominant negative mutant proteins (Herskowitz, 1987, *Nature* 329: 219–222).

Specifically, the tumor suppressor gene p53 was first discovered as an altered forms which encoded a mutant protein (Sap et al., 1986. *ibid.*; Weinberger et al., 1986, *ibid.*; Raycroft et al., 1990, *ibid.*; Milner et al., 1991, *Molec. Cell. Biol.* 11: 12–19). p53 is a tumor suppressor gene that mediates cell response to various types of stress leading the cell growth arrest, apoptosis or other responses (i.e. differentiation) through modulation of expression of p53-responsive genes. p53 pathway is inactivated in the majority of human cancers making its restoration a major goal of gene therapy. At the same time, p53 pathway determines sensitivity of several tissues to DNA damaging treatments, including chemotherapy and gamma radiation. Therefore, stimulation or restoration of the p53 pathway could be critically important for the efficacy of anti-cancer therapy, while suppression of p53 pathway could be used to defend sensitive tissues from genotoxic stress and for the generation of immortal cell lines also requiring p53 functional inactivation. Oncogenic mutant p53 protein forms functionally inactive complexes with the wild-type protein; such complexes fail to provide the normal negative regulatory function of the p53 protein (Herskowitz, 1986, ibid.; Milner et al., 1991, ibid.; Montenarh & Quaiser, 1989, Oncogene 4: 379–382; Finlay et al., 1988, Molec. Cell. Biol. 8: 531–539).

The discovery and analysis of new recessive genes involved in neoplastic transformation has been greatly accelerated through the use of genetic suppressor elements (GSEs), derived from such genes and capable of selectively suppressing their function. GSEs are dominant negative factors that confer the recessive-type phenotype for the gene to which the particular GSE corresponds. Recently, some developments have been made in the difficult area of isolating recessive genes using GSE technology. Roninson et al., U.S. Pat. No. 5,217,889 (issued Jun. 8, 1993) teach a generalized method for obtaining GSEs (see also Holzmayer et al., 1992, Nucleic Acids Res. 20: 711–717). Gudkov et al., 1993, Proc. Natl. Acad. Sci. USA 90: 3231–3235 teach isolation of GSEs from topoisomerase II cDNA that induce resistance to topoisomerase II-interactive drugs. Co-pending U.S. patent application Ser. No. 08/204,740, filed Mar. 2, 1994 disclosed the use of GSE technology to isolate neoplastic transformation-specific GSEs that were found to be derived from a variety of cellular genes previously unsuspected of any role in neoplastic transformation.

More recently, the GSE technology has been used to isolate and identify a new human tumor suppressor gene, termed ING1, that encodes a protein product termed $p33^{ING1}$ (see International Application, Publication No. WO97/21809, published Jun. 19, 1997). The ING1 gene encodes a nuclear protein $p33^{ING1}$, overexpression of which inhibits growth of different cell lines. The ING1 gene encodes a ubiquitously expressed, nucleus-localized zinc-finger protein that is highly conserved in evolution. Inhibition of ING1 gene expression, for example, by antisense RNA promotes anchorage independent growth in mouse breast epithelial cells and in Ela+ras-transformed mouse fibroblasts, while ING1 gene overexpression leads to G1 growth arrest in several cell lines tested. These properties (and others) of ING1 suggest its involvement in negative regulation of cell proliferation and in control of cellular aging, anchorage dependence and apoptosis (Garkavstev et al., 1996, Nature Genetics 14: 415–420; Garkavstev et al., 1997, Mol Cell Biol. 17: 2014–2019; Helbing et al., 1997, Cancer Res. 57: 1255–1258). This protein has been shown to be involved in negative regulation of mammalian cell proliferation and control of cellular aging, apoptosis and anchorage-dependent growth. These cellular functions have been recognized to depend largely on the activity of the p53 tumor suppressor gene described above (Gottlieb & Oren, 1996, Biochim. Biophys. Acta Rev. Cancer 1287: 77–102).

In addition, ING1 has been mapped to human chromosome 13q34 (Garkavstev et al., 1997, Cytogenet. Cell Genet. 76: 176–178; Zeremski et al., 1997, Somatic Cell Mol. Genet. 23: 233–236), and loss of heterozygosity in this chromosomal locus has been reported in squamous cell carcinomas of head and neck (Maestro et al., 1996, Cancer Res. 56: 1146–1150). Limited analysis of tumor cell lines revealed mutation of ING1 in neuroblastoma cell line and reduced expression in several breast carcinoma cell lines (Garkavstev et al., 1996, Nature Genetics 14: 415–420).

There remains a need in the art to characterize mammalian tumor suppressor genes to better understand the interrelatedness of the role(s) played by these genes in control of cell growth. More specifically, there is a need in the art to determine the interrelatedness of p33 and p53 in mediating their effects on control of cell growth and aging. In particular, there is a need in the art to understand how manipulation of $p33^{ING1}$ and/or p53 gene expression, using GSE- and recombinant DNA technologies, can be used to promote or inhibit cell growth where appropriate. There is a great need in the art to determine whether expression or lack of expression of $p33^{ING1}$ is related to neoplastic transformation and malignant disease, as has been shown for p53. Finally, there is a need in the art to establish whether a more complete assessment of a human patient for the risk of developing malignant or proliferative disease requires a determination of the status of both p53 and ING gene expression.

BRIEF SUMMARY OF THE INVENTION

The invention provides embodiments of nucleic acids encoding all or a portion of a mammalian gene, known as ING1 (see Garkavstev et al., 1996, Nature Genetics 14: 415–420) and methods for using such embodiments to enhance or inhibit the biochemical activity of the tumor suppressor gene known as p53 in mammalian cells. Specifically, the invention provides an embodiment of human ING1-encoding nucleic acids comprising an alternative splice variant of the ING1 gene that has been isolated from human spleen cDNA, and truncated variants thereof, as components of recombinant expression constructs capable of expressing said nucleic acids in mammalian cells. The invention also provides cells transformed with said recombinant expression constructs and expressing the alternative splice variant of the ING1 cDNA and methods for using such recombinant expression constructs for introducing nucleic acid encoding the alternative splice variant or truncated portions thereof into mammalian cells to inhibit transcriptional activator activity of p53.

In a first embodiment of this aspect of the invention is provided a nucleic acid encoding an alternative splice variant of human ING1. In a preferred embodiment, the nucleic acid has a nucleotide sequence encoding an amino acid sequence identified as SEQ ID No. 5 and shown in FIG. 7. This nucleic acid differs from the previously-reported ING1 sequence (see Garkavstev et al., 1996, ibid.) in encoding an amino acid sequence (SEQ ID No.: 5) having 25 fewer amino acids (269 vs. 294) and having a different amino acid sequence encoding the first 46 amino acids of the sequence (compare SEQ ID No. 3 and SEQ ID No. 5). The 269 amino acid residue protein produced from the alternative splice variant of ING1 is termed $p28^{ING1}$ herein.

In this aspect of the invention is also provided recombinant expression constructs containing nucleic acid encoding the alternative splice variant of the invention. Preferably, said recombinant expression constructs are operatively linked to the nucleic acid encoding the alternative splice variant of the invention, whereby the recombinant expression constructs are capable of expressing the gene product of the alternative splice variant of the invention in a cell, preferably a mammalian and most preferably a human cell. In particularly preferred embodiments, the recombinant expression construct comprises a retroviral vector containing a selectable marker gene.

The invention also provides cells, preferably mammalian and most preferably human cells, that have been transformed with the recombinant expression constructs of the invention and are capable of expressing the gene product of the alternative splice variant of the invention in the cell.

In a second embodiment if this aspect of the invention is provided a nucleic acid encoding a truncation variant of the human ING1 gene product. In preferred embodiments, the nucleic acid has a nucleotide sequence encoding an amino acid sequence identified as SEQ ID No. 7 and shown in FIG. 8. This truncation variant encodes 210 amino acids and is identical to the amino acid sequence from residue 59 to residue 269 of the amino acid sequence of the gene product of the alternative splice variant provided by the invention (compare SEQ ID No. 5 and SEQ ID No. 7). The 210 amino acid residue protein produced from the truncation variant of ING1 is termed $p26^{ING1}$ herein.

In this aspect of the invention is also provided recombinant expression constructs containing nucleic acid encoding the truncation variant of the human ING1 gene product. Preferably, said recombinant expression constructs are operatively linked to the nucleic acid encoding the truncation variant of the human ING1 gene product of the invention, whereby the recombinant expression constructs are capable of expressing the truncation variant of the human ING1 gene product of the invention in a cell, preferably a mammalian and most preferably a human cell. In particularly preferred embodiments, the recombinant expression construct comprises a retroviral vector containing a selectable marker gene.

The invention also provides cells, preferably mammalian and most preferably human cells, that have been transformed with the recombinant expression constructs of the invention and are capable of expressing the truncation variant of the human ING1 gene product in the cell.

The invention also provides methods for modulating the transcriptional activator activity of the tumor suppressor gene product, p53, in mammalian cells. Preferably, the methods of the invention provide for the introduction of nucleic acid species encoding the ING1 gene product, $p33^{ING1}$(SEQ ID No. 3), or most preferably the alternative splice variant of the invention (SEQ ID No. 5) or truncated variant thereof (SEQ ID No. 7) into a cell, preferably a mammalian cell and most preferably a human cell, wherein the transcriptional activity of p53 is enhanced thereby. Most preferably the methods of the invention comprise the step of introducing into the mammalian cell a recombinant expression construct of the invention that expresses the ING1 gene product, $p33^{ING1}$(SEQ ID No. 3), or most preferably the alternative splice variant of the invention (SEQ ID No. 5) or truncated variant thereof (SEQ ID No. 7). The invention thereby provides a method for enhancing p53-mediated transcription of a gene in a mammalian cell that expresses p53, the method comprising the step of introducing into the cell a recombinant expression construct encoding the ING1 gene product, $p33^{ING1}$(SEQ ID No. 3), or most preferably the alternative splice variant of the invention (SEQ ID No. 5) or truncated variant thereof (SEQ ID No. 7) of the invention.

In another aspect, the invention provides genetic suppressor elements (GSEs) that are random fragments derived from the ING1 gene (SEQ ID No. 2). The invention explicitly provides a particular GSE comprising an antisense RNA species that inhibits expression of ING1 in mammalian cells (SEQ ID No. 1), and methods for producing a multiplicity of GSEs from isolated ING1-encoding nucleic acid. Also provided by the invention are methods for inhibiting the growth-suppressing phenotype associated with expression of the INGC gene product, $p26^{ING1}$, by expression of such ING1-specific GSEs in mammalian cells using recombinant expression constructs. Cells transformed with said recombinant expression constructs are also provided.

In this aspect, the invention provides a genetic suppressor element (GSE) encoding an antisense RNA molecule having a nucleotide sequence identified as SEQ ID No. 1 and shown in FIG. 1. In preferred embodiments, the GSE is contained within a recombinant expression construct capable of directing transcription of the nucleic acid encoding the GSE in a mammalian cell. In particularly preferred embodiments, the recombinant expression construct comprises a retroviral vector containing a selectable marker gene. In this aspect of the invention is also provided a mammalian cell transformed with said recombinant expression construct that is capable of expressing the GSE in the cell.

In another embodiment of this aspect of the invention is provided a method of identifying genetic suppressor elements derived from the $p33^{ING1}$ gene. The method comprises to steps of:

(a) generating a set of random fragments of cDNA or genomic DNA fragment encoding the $p33^{ING1}$ gene;

(b) transferring these DNA fragments to an expression vector to yield a library, wherein the expression vector is capable of expressing the DNA fragments in a living cell;

(c) genetically modifying living cells by introducing the random fragment library of step (b) into the living cells, wherein the living cells are growth-inhibited due to expression of the $p33^{ING1}$ gene product in the cells;

(d) isolating or enriching for genetically modified living cells containing $p33^{ING1}$ gene-derived genetic suppressor elements by selecting cells that are no longer growth inhibited; and (e) obtaining the genetic suppressor element from the genetically modified cells.

Also provided by the invention are GSEs produced by this method, wherein said GSEs comprise nucleic acids encoding antisense RNA species of the ING1 gene and peptide fragments of the $p33^{ING1}$ gene product. The invention also provides synthetic oligonucleotides having a nucleotide sequence from about 12 nucleotides to all of the nucleotide sequence of an antisense RNA encoded by a GSE produced by the methods of the invention. The invention also provides synthetic peptides having an amino acid sequence corresponding to from about 6 amino acids to all of the amino acids encoded by the nucleotide sequence of a GSE produced according to the methods of the invention.

In yet another aspect of the invention are provided methods for inhibiting the growth-inhibited phenotype of a mammalian cell expressing the $p33^{ING1}$ gene product, said methods comprising the step of introducing into the mammalian cell a recombinant expression construct of the invention that expresses a GSE derived from the ING1 gene or the $p33^{ING1}$ gene product. In a preferred embodiment, the recombinant expression construct encodes the GSE disclosed in FIG. 1 and identified by SEQ ID NO. 1. In other preferred embodiments, the recombinant expression construct encodes a GSE produced from the ING1 gene according to the methods of the invention. In one aspect of the methods of the invention is provided a method for inhibiting apoptosis in a mammalian cell, the method comprising the step of introducing into the cell a recombinant expression construct encoding a genetic suppressor element of the invention. In another aspect, the invention provides a method for delaying cellular senescence in a mammalian cell, comprising the step of introducing into the cell a recombinant expression construct encoding a genetic suppressor element of the invention. In yet another aspect, the invention provides a method for facilitating anchorage independent growth in a mammalian cell, the method comprising the step of introducing into the cell a recombinant expression construct encoding a genetic suppressor element of the invention. In still another aspect, the invention provides a method for protecting a mammalian cell from radiation or cytotoxic drugs, the method comprising the step of introducing into the cell a recombinant expression construct encoding a genetic suppressor element of the invention. The invention also provides a method for inhibiting p53-mediated transcription of a gene in a mammalian cell that expresses p53, the method comprising the step of introducing into the cell a recombinant expression construct encoding a genetic suppressor element of the invention.

In another aspect, the invention also provides methods for determining the expression status of $p33^{ING1}$ in cells and tissues of an animal, whereby reduced or absent expression of this protein is an indication that the animal carries or is at risk of developing a malignant disease.

In this aspect, the invention provides methods for detecting and characterizing expression of the ING1 gene and $p33^{ING1}$ gene product in cell or tissue samples from an animal, most preferably a human, specifically for detecting reduced or absent expression of the ING1 gene and $p33^{ING1}$ gene product related to the existence of malignant or premalignant disease or condition, or the risk of developing malignant disease, in the animal. In preferred embodiments, the method comprises the step of obtaining a cell or tissue sample from a human and assaying the sample to determine the level or amount of ING1 gene expression in the sample. In preferred embodiments, the method also comprises the step of obtaining a normal cell or tissue sample from the human for providing a comparison, wherein reduced or absent expression of the ING1 gene and $p33^{ING1}$ gene product in the cell or tissue sample, when compared with expression of the ING1 gene and $p33^{ING1}$ gene product in the normal cell or tissue sample from the human, indicates the existence of malignant or premalignant disease or condition, or a risk of developing a malignant disease. The methods of the invention are provided as diagnostic methods for individuals having signs or symptoms of malignant disease, assessment methods for determining the risk of developing a malignant or premalignant condition in an individual, and screening methods for detecting a malignant or premalignant condition in an individual. In preferred embodiments, the malignant or premalignant disease or condition is gastric cancer, breast cancer, brain cancer, or head or neck squamous cell carcinoma. The invention provides such methods for detecting ING1 gene expression levels by assaying the cell or tissue sample for the level or amount of ING1-encoding mRNA species expressed in the cell or tissue sample or by assaying the cell or tissue sample for the level or amount of $p33^{ING1}$ gene product produced by the cell or tissue sample.

In alternative and preferred embodiments of this aspect of the methods of the invention are provided methods having the additional step of assaying the cell or tissue sample to determine the level or amount of p53 gene expression in the sample, wherein reduced or absent expression of p53 and $p33^{ING1}$ indicates the existence of malignant or premalignant disease or condition, or a risk of developing a malignant disease.

Specific preferred embodiments of the present invention will become evident from the following more detailed description of certain preferred embodiments and the claims.

BRIEF DESCRIPTION OF THE DRAWINGS

FIG. 1 shows the nucleotide sequence (SEQ ID No. 1) of an 182 basepair genetic suppressor element specific for ING1.

FIGS. 2A through 2C depict the nucleotide (SEQ ID No. 2) and amino acid (SEQ ID No. 3) sequences of a cDNA molecule encoding $p33^{ING1}$.

FIG. 4A shows growth inhibition assays in variants of p53-null Balb/c 3T3 cells. The first row illustrates immunofluorescent staining of cultures of such cells transduced with vector, with an ING/-encoding retroviral construct, or with an anti-ING1 GSE-encoding retroviral construct, stained with an anti-$p33^{ING1}$ antibodies. The second row illustrates cultures of each of these cell variants transduced with a wild type p53-encoding construct. The third row illustrates cultures of each of these cell variants transduced with a mutant $p53^{175His}$-encoding construct. Each of these vectors also contains a hygromycin resistance gene and is selected in hygromycin.

FIG. 4B shows p53-null Balb/c 3T3 cell cultures transfected with a wild type p53-encoding retroviral vector, co-transfected with this construct+a retroviral vector encoding an anti-p53 GSE, termed GSE56 (see Ossovskaya et al., 1996, *Proc. Natl. Acad Sci. USA* 93: 10309–10314), or co-transfected with the wild type p53-cncoding construct + a retroviral vector encoding an anti-$p33^{ING1}$ GSE.

FIGS. 7A and 7B depict the nucleotide (SEQ ID No. 4) and amino acid (SEQ ID No. 5) sequences of an alternatively-spliced cDNA molecule encoding an alterative ING1 gene product termed $p28^{ING1}$.

FIG. 8 depicts the nucleotide (SEQ ID No. 6) and amino acid (SEQ ID No. 7) sequences of a truncated variant of the alternatively-spliced cDNA molecule of the invention termed $p26^{ING1}$.

DETAILED DESCRIPTION OF THE PREFERRED EMBODIMENTS

Figure 3A:
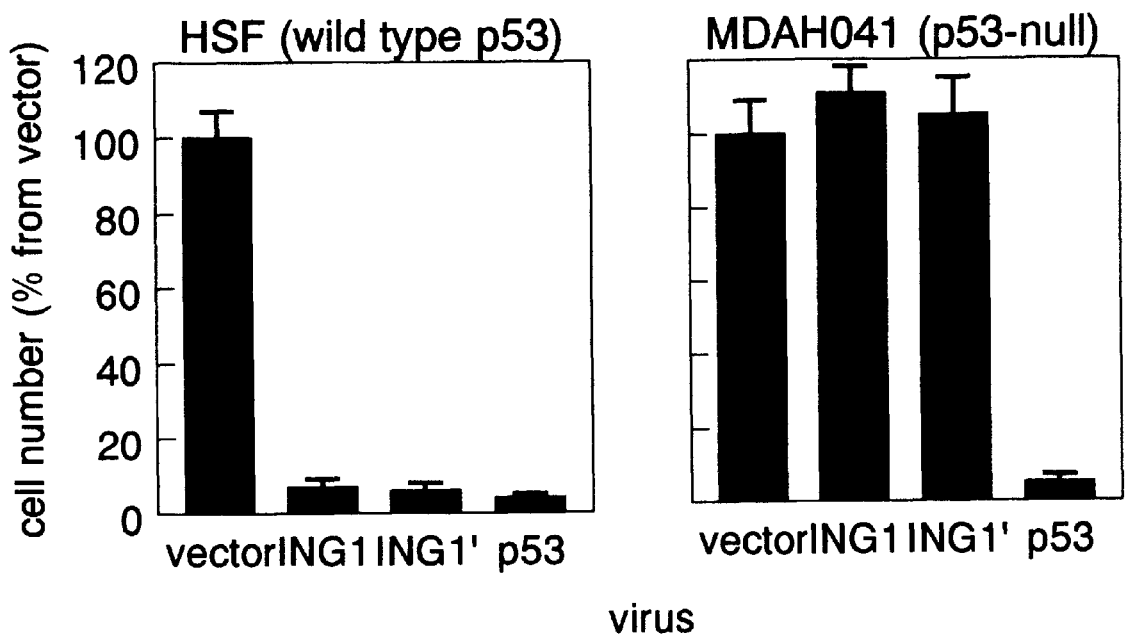
FIG. 3A illustrates a pair of graphs showing the number of surviving cells (either human skin fibroblasts (HSF) or the Li-Fraumeni derived cell line MDAH041) after transduction with a retroviral vector encoding $p28^{ING1}$ (ING1), $p26^{ING1}$ (ING1'), p53 or the retroviral vector itself. Cells were infected with retrovirus and selected using 500 μg/mL G418 (a mammalian neomycin analogue, available from GIBCO, Rockville, Md.) or 200 μg/mL hygromycin (obtained from Sigma Chemical Co., St. Louis, Mo.) and counted using the MTT assay (see Pauwels et al., 1988, *J. Virol. Methods* 20: 309–321).

The present invention is based on the discovery that the biological effects of ING1 and p53 gene expression are interrelated and require the activity of both genes. Specifically, the present inventors have discovered that neither of these two genes can, on it's own, cause growth inhibition when the other one is suppressed. Expression of both genes in a mammalian cell results in normal growth regulation anchorage-dependent growth and apoptosis as a response to irreversible DNA damage and other cellular insult. Inhibition of expression of either gene results in a loss of cellular growth control, anchorage-independent growth, inhibition of apoptosis and resistance to radiation and cytotoxic drugs.

Furthermore, a key mechanism of p53-mediated growth control, activation of transcription of certain cellular genes (such as the WAF1 gene), depends on the expression of ING1. In addition, a physical association between $p33^{ING1}$ and p53 proteins is disclosed as detected by immunoprecipitation. These results indicate that $p33^{ING1}$ is a component of the p53 signaling pathway that cooperates with p53 in negative regulation of cell proliferation by modulating p53-dependent transcriptional activation. Biological function of p53 signaling pathway is therefore can be regulated (both enhanced or suppressed) by modulating $p33^{ING1}$ activity.

Expression of exogenous ING1 cDNA introduced into cells expressing p53 produces arrest of the cells in the G1 phase of the cell cycle. Several cell types respond to introduction and expression of ING1 cDNA with apoptosis, and ING1 gene expression has been found to be up regulated (i.e., increased) in senescent human fibroblasts (Garkavstev et al., 1997, *Mol. Cell Biol.* 17: 2014–2019). Inhibition of ING1 expression by antisense RNA (such as the genetic suppressor element (GSE) identified as SEQ ID No. 1) promotes anchorage independent growth in mouse breast epithelial cells, increases the frequency of focus formation of NIH 3T3 cells, and prolongs the life span of diploid human fibroblasts in culture.

In addition, the key role of $p33^{ING1}$ in the p53 signaling pathway opens the possibility of regulation of this pathway activity by modulating $p33^{ING1}$ activity. Such regulation may involve enhancement or restoration of p53 function by increasing the activity of $p33^{ING1}$, or suppression of p53 function by inhibition of $p33^{ING1}$. Stimulation or restoration of the p53 pathway is critically important for the efficacy of anti-cancer therapy, while suppression of p53 pathway can be used to defend sensitive tissues from genotoxic stress and for the generation of immortal cell lines also requiring p53 functional inactivation. All the above applications can be achieved by modulation of $p33^{ING1}$ activity, as an alternative to modulation of the activity of p53 itself. The discovery that $p33^{ING1}$ is an essential component of p53 signaling pathway provides a novel approach to regulation of the p53 pathway in mammalian cells.

Thus, this invention is based in the present inventor's finding that cell growth inhibition is mediated at least in part by the expression of $p33^{ING1}$ in mammalian cells, i.e., cell growth decreases as expression of $p33^{ING1}$ increases, and cell growth increases as expression of $p33^{ING1}$ decreases.

This invention provides a novel alternative splice variant of the human ING1 gene provided as a cDNA isolated from a human spleen cDNA library. Analysis of human and other animal tissues and cells indicates that this alternative splice variant is ubiquitously expressed in all cells and tissues tested, and the invention thus provides nucleic acid encoding this alterative splice variant isolated from any cell or cell type from any mammalian species. The amino acid sequence encoded by this alternative splice variant differs from the cDNA encoding $p33^{ING1}$ reported in Garkavstev et al. (1996, *ibid.*) in two ways. First, the alternative splice variant encodes a gene product that is about 25 amino acids shorter than $p33^{ING1}$ and having a predicted molecular weight of about 28 kilodaltons (accordingly, the gene product of this alterative splice variant is termed $p28^{ING1}$ herein). Secondly, the amino acid sequence of the alternative splice variant gene product has a sequence significantly different from the first 61 amino acids of the $p33^{ING1}$ sequence for the first 46 amino acids of the $p28^{ING1}$ sequence (compare SEQ ID No. 3 and SEQ ID No. 5). These results indicated that the first 46 amino acid residues of the $p28^{ING1}$ sequence are encoded by at least one exon different from the exon(s) used to encode the first 61 amino acids of the $p33^{ING1}$ sequence.

The invention thus provides two novel, alterative embodiments of the gene products of the ING1 gene: an alterative splice variant (termed $p28^{ING1}$ and identified by SEQ ID No. 5) that differs in amino acid sequence from the $p33^{ING1}$ gene product reported by Garkavstev et al, and a truncated variant thereof (termed $p26^{ING1}$ and identified by SEQ ID No. 7).

The invention also provides a genetic suppressor element (GSE) comprising a 182 base pair nucleic acid, the sequence of which is shown in FIG. 1 and identified as SEQ ID No. 1. The invention also provides a method for producing additional GSEs from the ING1 gene sequence (shown in FIG. 2 and identified as SEQ ID No. 2). The invention also provides a method of decreasing $p33^{ING1}$ expression in a mammalian cell by introducing the GSE identified as SEQ ID No. 1 or other GSEs produced by the methods of the invention in a manner that allows the cell to produce the GSE.

The nucleic acids provided by the invention, including nucleic acids encoding the alternative splice variant (exemplified by the nucleic acid identified by SEQ ID No. 4), the truncated variant thereof (exemplified by the nucleic acid identified by SEQ ID No. 6) and GSEs (exemplified by the nucleic acid identified by SEQ ID No. 1) may be synthesized in host cells transformed with a recombinant expression construct comprising the nucleic acid. Such recombinant expression constructs also advantageously comprise a vector that is a replicable DNA construct. Vectors are used herein either to amplify DNA encoding the nucleic acid and, most preferably, express DNA which encodes the GSE or amino acid sequence of the alternative splice variant or truncated version thereof. For the purposes of this invention, a recombinant expression construct is a replicable DNA construct in which a DNA sequence encoding a GSE or amino acid sequence of the alternative splice variant or truncated version thereof is operably linked to suitable control sequences capable of effecting the expression of the GSE in a suitable host. For the purposes of this invention, the term "operably linked" in intended to indicate that the nucleic acid components of the recombinant expression construct are linked, most preferably covalently linked, in a manner and orientation that the nucleic acid sequences encoding a GSE or amino acid sequence of the alternative splice variant or truncated version thereof are under the control of and respond to the transcriptional, replication and other control elements comprising the vector construct when introduced into a cell, preferably a mammalian cell and most preferably a human cell. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants. See, Sambrook et al., 1990, *Molecular Cloning: A Laboratory Manual* (Cold Spring Harbor Press: New York).

Preferably, the nucleic acids of the invention are cloned into and expressed using the MoMLV-based retroviral vector pLNCX, which carries the neo (G418 resistance) gene, transcribed from the promoter contained in the retroviral long terminal repeat (LTR), and which expresses the inserted sequence from a strong promoter of the cytomegalovirus (CMV) (see FIG. 2 of co-pending U.S. Ser. No. 08/486,382, filed Jun. 6, 1995, now U.S. Pat. No. 5,866,327 and incorporated by reference in its entirety). Additional vectors for preparing the recombinant expression constructs of the invention include plasmids, viruses (including phage), retroviruses, and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. Suitable vectors also comprise additional or alternative selectable marker sequences, such as sequences conferring resistance to hygromycin or other antibiotic substances, or sequences encoding a gene that complements a cellular deficiency (such as thymidine kinase or dihydrofolate reductase).

Transformed host cells are cells which have been transformed or transfected with recombinant expression constructs made using recombinant DNA techniques and comprising sequences encoding GSEs or amino acid sequences of the alternative splice variant or truncated version thereof sequences. Mammalian cells are preferred, as illustrated in the Examples.

For the purposes of this invention, the term "ING1 gene" and "$p33^{ING1}$" will be understood to encompass any ING1 gene, particularly mammalian, and preferably mouse or human, ING1 gene. The instant invention also provides alternative splice variants of the ING1 gene encoding a novel gene product, termed $p28^{ING1}$ and having an amino acid sequence identified as SEQ ID No. 5. For the purposes of this invention, the term "$p28^{ING1}$" will be understood to encompass any alternative splice variant of an ING1 gene, particularly mammalian, and preferably mouse or human, ING1 gene. The instant invention also provides a truncated version of the alternative splice variants of the ING1 gene encoding yet another novel gene product, having an amino acid sequence identified as SEQ ID No. 7. For the purposes of this invention, the term "truncated version of $p28^{ING1}$" will be understood to encompass any such variant of an ING1 gene, particularly mammalian, and preferably mouse or human, ING1 gene. The invention also provides GSEs derived from any ING1 gene or any alternative splice variant or truncated version thereof. The invention specifically is intended to contain within its scope all ING1 genes and GSEs derived therefrom that are capable of overcoming growth inhibition in a mammalian cell.

The term "growth inhibition phenotype" is intended to encompass a plelotropic phenotype in a mammalian cell, including but not limited to growth inhibition (including contact inhibition), cellular aging and senescence, apoptosis, sensitivity to radiation and cytotoxic drugs, and anchorage-dependent growth.

The GSEs identified by the methods of the invention will be homologous to a $p33^{ING1}$ gene. For purposes of the invention, the term "homologous to" a $p33^{ING1}$ gene has two different meanings, depending on whether the GSE acts through an antisense mechanism or antigene mechanism (i.e., through a mechanism of interference at the protein level). In the former case, a GSE that is an antisense or antigene oligonucleotide or polynucleotide is homologous to a gene if it has a nucleotide sequence that hybridizes under physiological conditions to the gene or its mRNA transcript by Hoogsteen or Watson-Crick base-pairing. In the latter case, a GSE that interferes with a protein molecule is homologous to the gene encoding that protein molecule if it has an amino acid sequence that is the same as that encoded by a portion of the gene encoding the protein, or that would be the same, but for conservative amino acid substitutions. In either case, as a practical matter, whether the GSE is homologous to a gene is determined by assessing whether the GSE is capable of inhibiting or reducing the function of the gene; in particular, any $p33^{ING1}$ gene, preferably any mouse or human $p33^{ING1}$ gene, as disclosed herein.

The method of identifying and isolating $p33^{ING1}$-specific GSEs provided by the invention comprises the step of screening a $p33^{ING1}$-specific cDNA or $p33^{ING1}$-specific genomic DNA random fragment expression library phenotypically to identify clones that are no longer growth inhibited or are resistant to radiation or cytotoxic drugs. Preferably, the library of random fragments of $p33^{ING1}$ specific cDNA or $p33^{ING1}$-specific genomic DNA is cloned into a retroviral expression vector. In this preferred embodiment, retrovirus particles containing the library are used to infect cells and the infected cells containing $p33^{ING1}$-specific GSEs are identified by overgrowth of growth-inhibited cells or by survival in a concentration of a DNA damaging agent that kills uninfected cells. Preferably, the inserts in the library will range from about 100 b.p. to about 700 b.p. and more preferably, from about 200 b.p. to about 500 b.p. Once a clonal population of such cells has been isolated, the library clone encoding the GSE is rescued from the cells. At this stage, the nucleotide sequence of the insert of the expression library may be determined; in clones derived from a $p33^{ING1}$ gene-specific cDNA random fragment expression library, the nucleotide sequence is expected to be homologous to a portion of the $p33^{ING1}$ gene nucleotide sequence. Alternatively, the rescued library clone may be further tested for its ability to release naive cells from growth control or to confer resistance to DNA damaging agents and cytotoxic drugs in additional transfection or infection and selection assays, prior to nucleotide sequence determination. Determination of the nucleotide sequence, of course, results in the identification of the GSE.

Thus, the invention also provides a method for obtaining ING1 gene-derived GSEs having optimized suppressor activity. By screening a random fragment expression library made exclusively from ING1 gene-specific fragments, a much greater variety of GSEs derived specifically from the ING1 gene can be obtained, compared with a random fragment library prepared from the subtractive cDNA library disclosed in International Application, Publication No. WO97/21809. Consequently, the likelihood of obtaining optimized GSEs, i.e., those ING1-derived GSEs conferring an optimal level of release naive cells from growth control or resistance to DNA damaging agents and cytotoxic drugs, is maximized using the single gene random fragment library approach.

The invention also provides synthetic peptides and oligonucleotides that are capable of inhibiting the function of $p33^{ING1}$. Synthetic peptides according to the invention have amino acid sequences that correspond to amino acid sequences encoded by GSEs according to the invention. Synthetic oligonucleotides according to the invention have nucleotide sequences corresponding to the nucleotide sequences of GSEs according to the invention. Once a GSE has been discovered and sequenced, and its orientation is determined, it is straightforward to prepare an oligonucleotide corresponding to the nucleotide sequence of the GSE (for antisense-oriented GSEs) or amino acid sequence encoded by the GSE (for sense-oriented GSEs). In certain embodiments, such synthetic peptides or oligonucleotides may have the complete sequence encoded by the GSE or may have only part of the sequence present in the GSE, respectively. In certain other embodiments, the peptide or oligonucleotide may have only a portion of the GSE-encoded or GSE sequence. In such latter embodiments, undue experimentation is avoided by the observation that many independent GSE clones corresponding to a particular gene will have the same 5' or 3' terminus, but generally not both. This suggests that many GSE's have one critical endpoint, from which a simple walking experiment will determine the minimum size of peptide or oligonucleotide necessary to inhibit gene function. For peptides, functional domains as small as 6–8 amino acids have been identified for immunoglobulin binding regions. Thus, peptides or peptide mimetics having these or larger dimensions can be prepared as GSEs. For antisense oligonucleotides, inhibition of gene function can be mediated by oligonucleotides having sufficient length to hybridize to their corresponding mRNA under physiological conditions. Generally, oligonucleotides having about 12 or more bases will fit this description. Preferably, such oligonucleotides will have from about 12 to about 100 nucleotides. As used herein, the tern oligonucleotide includes modified oligonucleotides having nuclease-resistant internucleotide linkages, such as phosphorothioate, methylphosphonate, phosphorodithioate, phosphoramidate, phosphotriester, sulfone, siloxane, carbonate, carboxymethylester, acetamidate, carbamate, thioether, bridged phosphoramidate, bridged methylene phosphonate and bridged phosphorothioate internucleotide linkages. The synthesis of oligonucleotides containing these modified linkages is well known in the art. (See, e.g., Uhlmann and Peyman, 1990, Chemical Reviews 90: 543–584; Schneider and Banner, 1990, Tetrahedron Letters 31: 335). The term oligonucleotides also includes oligonucleotides having modified bases or modified ribose or deoxyribose sugars.

The invention also provides diagnostic methods for determining the presence of a malignant or premalignant disease or condition in a human, or in assessing the risk of developing a malignant condition in an individual. Reduced or absent expression of ING1 provides the basis for such a diagnostic assay for malignant or premalignant disease or condition, or for assessing the risk of developing such a malignant or premalignant condition in an individual. For the purposes of this invention, the term "ING1 gene expression" or variations thereof is intended to encompass expression of all forms and variants, particularly including splice variants, of the ING1 gene, and specifically including $p33^{ING1}$, $p28^{ING1}$ and $p26^{ING1}$ as defined herein. Also for the purposes of this invention, reference to "$p33^{ING1}$" is intended to refer equally to $p28^{ING1}$ and $p26^{ING1}$ as defined herein, unless otherwise explicitly stated. For the purposes of this invention, the term "malignant or premalignant condition" is intended to encompass frank malignancy, including any of the known variety of cancers, and most preferably breast cancer, gastric cancer, head and neck squamous cell carcinoma, and brain cancers including astrocytomas, meningiomas, and glioblastomas, and neuroblastomas. Also encompassed by this term are premalignant lesions, carcinoma in situ, and any of a variety of occult, asymptomatic, noninvasive precancerous conditions known to place an individual art risk for developing frank malignant disease. A first embodiment of a diagnostic assay according to this aspect of the invention utilizes an oligonucleotide or oligonucleotides that is/are homologous to the sequence of the ING1 gene. In this embodiment, RNA is extracted from a cell or tissue sample, and RNA specific for the ING1 gene is quantitated by standard filter hybridization procedures, an RNase protection assay, or by quantitative cDNA-PCR (see Noonan et al., 1990, Proc. Natl. Acad. Sci. USA 87: 7160–7164). In a second embodiment of a diagnostic assay according to this aspect of the invention, antibodies produced against the ING1 gene product, $p33^{ING1}$, are used in a conventional quantitative immunoassay (e.g., RIA or immunohistochemical assays) to determine the amount of the gene product of interest present in a sample of proteins extracted from the cell or tissue sample to be tested, or on the surface or at locations within the tested cells or tissues. Antibodies useful in this aspect of the invention are polyclonal antibodies and antisera as disclosed in International Application, Publication No. WO97/21809, or monoclonal antibodies produced by conventional methods known to those with skill in the art.

In alternative embodiments, the diagnostic methods of the invention also include the steps of assaying a cell or tissue sample for expression of p53 as well as expression Of $p33^{ING1}$. Antibodies specific for p53 for detecting p53 protein are available in the art, as are specifically hybridizing sequences and amplification primers for detecting p53 mRNA expression, as disclosed in Ossovskaya et al., 1996, Proc. Natl. Acad. Sci. USA 93: 10309–10314 (incorporated by reference).

Specific preferred embodiments of the present invention will become evident from the following more detailed description of certain preferred embodiments and the claims.

EXAMPLE 1

Isolation of ING Gene

The nucleic acid (SEQ ID No. 2) and amino acid (SEQ ID No. 3) of the human ING gene and $p33^{ING1}$ gene product are shown in FIG. 2 and were isolated as described in International Application, Publication No. WO97/21809, published Jun. 19, 1997, and in Garkavstev et al., 1996, Nature Genetics 14: 415–420, the disclosures of each of which are incorporated by reference in their entirety herein. The complete coding sequence of the $p33^{ING1}$ gene product was cloned into the pLNCX retroviral cloning vector (described in co-pending U.S. Ser. No. 08/204,740, incorporated by reference) using conventional methods (see Sambrook, et al., ibid.).

The truncated version of the gene product of the ING1 gene was produced using conventional techniques (Sambrook et al., ibid.) by cloning a portion of the nucleic acid identified as SEQ ID No. 2 into a recombinant expression construct so that the first initiation codon in the sequence is methionine-85 in SEQ ID No. 3. The nucleotide sequence of the nucleic acid encoding the truncation variant termed $p26^{ING1}$ herein is shown in FIG. 8 and identified as SEQ ID No. 6, and the amino acid sequence of the protein produced thereby is shown in FIG. 8 and identified as SEQ ID No. 7.

EXAMPLE 1A

Isolation of Alternative Splice Variant of the ING Gene

The nucleic acid (SEQ ID No. 4) and amino acid (SEQ ID No. 5) of an alternative splice variant of the human ING gene are shown in FIGS. 7A and 7B were isolated as follows.

A partial mouse cDNA clone encoding the mouse homologue of the ING1 gene was obtained by screening a mouse embryo fibroblast cDNA library using conventional techniques (Sambrook et al., ibid.) and probed with a portion of the human ING1 cDNA identified by SEQ ID No. 2. The remainder of the mouse ING1 cDNA was obtained using a mouse RACE amplification kit specific for mouse spleen cDNA (Marathon®, obtained from Clonetech, Palo Alto, Calif.) and using amplification primers derived from the partial mouse cDNA clone obtained from the library screening. A particular band corresponding to the omitted 5' sequences was identified and used to obtain a full-length mouse cDNA clone encoding the mouse homologue of the ING1 gene.

The RACE amplification kit was used (specific for human spleen cDNA) analogously o produce the corresponding 5' sequences of human ING1 cDNA. When nucleic acid encoding these sequences were isolated and their nucleotide sequence determined and compared with the previously-disclosed human ING1 cDNA, it was found that this clone corresponded to a alternative splice variant that differed from the previously-disclosed sequence identified as SEQ ID No. 3 and described in Example 1 above. The RACE produced cloned 5' specific sequence of the alternative splice variant cDNA overlapped with the previously-disclosed cDNA sequence, thereby establishing the extent of the differences between the two species. A recombinant expression construct was produced by enzymatically splicing the RACE-produced 5' sequences specific for the alternative splice variant with the 3' specific sequences shared by these two ING1 cDNA species. Nucleotide sequence analysis determined that the amino acid sequence encoded by this cDNA was 25 amino acid residues shorter than the amino acid sequence encoded by the previously-reported ING1 transcript (shown here as SEQ ID No. 3) and that the first 46 amino acids of the cDNA isolated herein were different from the first 61 amino acids encoded by the cDNA previously reported as described in Example 1 (compare SEQ ID No. 3 and SEQ ID No. 5). These results indicated that this cDNA encoded an alternative splice variant of the human ING1 gene. The existence of the alternative splice variant in human spleen was confirmed using reverse transcription-polymerase chain reaction assay (Kawasaki & Wang, 1989, in PCR Technology, (Erlich, ed.), Stockton Press: New York, pp. 89–98). This construct produced $p28^{ING1}$ in mammalian cells.

All experiments described in the remaining examples were performed using the recombinant expression constructs encoding $p28^{ING1}$ or $p26^{ING1}$ or both.

EXAMPLE 2

Growth Suppressive Effect of $p33^{ING1}$ Depends on the Status of p53

In order to assess the relatedness of p33 and p53 expression in controlling growth and proliferation in mammalian cells, the effects of expressing $p28^{ING1}$ and/or $p26^{ING1}$ in cells differing in the status of p53 gene expression were assayed. It was expected that expression of ING1 would result in growth inhibition of the cells if the effects of ING1 were independent of p53 gene expression.

Cloned $p28^{ING1}$ and/or $p26^{ING1}$-encoding DNA was introduced into cells by retroviral transduction of either the truncated version of ING1 cDNA, the alternative splice variant of ING1 cDNA, or an antisense-oriented ING1 cDNA fragment (anti-ING1 GSE) comprising nucleotides 942–1124 of the ING1 cDNA sequence (SEQ ID No. 1), which acts as a potent inhibitor of $p26^{ING1}$ expression. Suppression of colony foliation by ING1 overexpression was evident only in the cells that maintained wild type p53, including human diploid skin fibroblasts (shown in FIG. 3A), primary mouse embryo fibroblasts and rat REF52 cells. After ING1 transduction, surviving cells expressed very low levels of $p28^{ING1}$, as determined by immunohistochemical staining and Western blot analysis. However, retroviral transduction of ING1 resulted in no growth suppressive effect in cells having inactivated p53. ING1-expression did not inhibit colony formation in human fibroblasts carrying a homozygous deletion of p53 (Li-Fraumeni fibroblasts, cell line MDAH041, obtained from George Stark), shown in FIG. 3A, nor in mouse embryo fibroblasts and REF52 cells that expressed a carboxyl-terminal portion of p53 (comprising GSE 56, as disclosed in Ossovskaya el al., 1996, Proc. Natl. Acad. Sci. USA 93: 10309–10314, incorporated by reference), that is a strong inhibitor of p53 function. In all cells tested, transduced ING1 was expressed at high levels, as shown in FIG. 4. These results indicated that cell growth inhibition mediated by $p28^{ING1}$ or $p26^{ING1}$ expression required co-expression of p53.

Figure 3B:
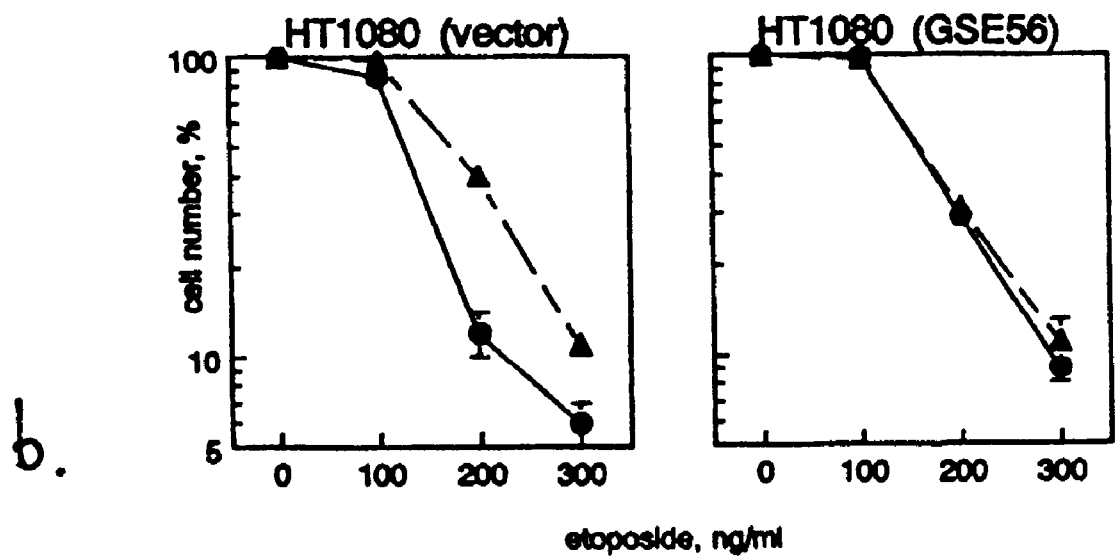
FIG. 3B depicts a pair of graphs showing the number of surviving HT1080 fibrosarcoma cells at increasing concentrations of etoposide, the cells having been infected with a retroviral vector cencoding $p28^{ING1}$ (ING1), $p26^{ING1}$ (ING1'), and either the retroviral vector itself or such a vector encoding GSE56, a genetic suppressor element encoding a portion of the carboxyl terminus of p53 that is a potent inhibitor of p53 function.

In another series of experiments, the effect of $p28^{ING1}$ expression was observed in a human fibrosarcoma cell line, HT1080 (available from the American Type Culture Collection, Accession No. CCL121). HT1080 cells ($10^5$ cells per well of a 6-well plate) transduced with different retroviral constructs were incubated in the presence of different concentrations of etoposide for 4 days. Cell viability was the determined using the MTT assay (Pauwels et al., 1988, J. Virol. Methods 20: 309–321). The experiment was repeated three times using three parallel wells for each drug concentration. In contrast to the result obtained with "normal" fibroblasts described above, overexpression of $p28^{ING1}$ in these cells had only a minor negative effect on colony growth under normal cell culture conditions. However, $p28^{ING1}$ expression strongly increased sensitivity of these cells to DNA damaging agents such as the chemotherapeutic drug etoposide or gamma irradiation. This effect was also found to be p53-dependent, since co-expression of the p53 suppressor GSE56 with $p28^{ING1}$ inactivated the sensitizing effect of DNA damaging agents produced in these cells by $p28^{ING1}$ expression alone. These results are shown in FIG. 3B, and are consistent with results showing that loss of p53 expression leads to resistance to radiation and chemotherapeutic drugs due to suppression of apoptosis (see Lowe et al., 1993, Cell 74: 957–967).

These observations indicate that the growth inhibitory effect of $p28^{ING1}$ or $p26^{ING1}$ expression requires wild type p53 gene expression and suggested that the ING1 gene product could act either "upstream" of or in cooperation with p53.

EXAMPLE 3

Growth Suppressive Effect of p53 Depends on the $p33^{ING1}$

The results disclosed above showed that the growth-inhibiting function Of $p33^{ING1}$ required the co-expression of p53 in mammalian cells. These results indicated that it was necessary to determine the converse: whether the phenotype associated with p53 expression—growth arrest and/or apoptosis - requires co-expression of p33$^{ING1}$.

In these experiments, variants of p53-deficient derivatives of mouse Balb/c 3T3 cells (termed 10(1) cells) were prepared that differed dramatically in p26$^{ING1}$ expression. One variant was transduced with the pLNCX retroviral vector alone, thereby expressing the endogenous amount of mouse p33$^{ING1}$. Another variant was transduced with the pLNCX retroviral vector encoding human p28$^{ING1}$, so that these cells expressed both the endogenous mouse p33$^{ING1}$ and the transduced human p28$^{ING1}$. The third variant was transduced with the pLNCX retroviral vector encoding the anti-ING1 GSE disclosed in Example 1 and shown in FIG. 1 (SEQ ID No. 1), so that expression of the endogenous mouse p33$^{ING1}$ was suppressed in these cells. Expression status of p33$^{ING1}$/p28$^{ING1}$ in each of these cell variants was determined by immunofluorescence staining using a chemiluminescence-labeled sandwich assay comprising a polyclonal rabbit anti-p33$^{ING1}$ antibody (prepared as described below) as primary antibody, a biotinylated donkey anti-rabbit antibody (SOURCE) a secondary antibody, and horse radish peroxidase-conjugated streptavidin (Amersham, Arlington Heights, Ill.); results of these assays are shown in FIG. 4A.

Into these cells was transduced a retroviral vector encoding a hygromycin resistance gene and either wild type p53 protein or a nonfunctional mutant, p53$^{175His}$ (as disclosed in Kopnin el al., 1995, Oncol. Res. 7: 299–306). The results of these experiments are shown in FIG. 4A. The cells were found to be highly sensitive to expression of exogenously-added p53 cDNA. Wild type p53 gene expression inhibited cell growth in variants expressing endogenous mouse p33$^{ING1}$ and the combination of mouse p33$^{ING1}$ and human p28$^{ING1}$. However, expression of p53 in cells co-expressing the anti-ING1 GSE were not growth-inhibited, and produced multiple colonies upon culturing (see FIG. 4A). incubation These results were expected, since the results of the experiments described in Example 2 indicated that p53 required functional p33$^{ING1}$ in order to mediate growth inhibition.

In contrast, no cell growth suppression was observed in any of the variants expressing the non-functional p53 mutant, p53$^{175His}$. Each of the variant cell cultures showed robust growth after transduction with retroviral vector encoding this mutant p53 species. These results, and in particular the results obtained with the variants expression either the endogenous mouse p33$^{ING1}$ or both the endogenous mouse p26$^{ING1}$ and the transduced human p28$^{ING1}$ showed that the growth-suppressing activity Of p33$^{ING1}$ requires co-expression of functional p53.

Cell rescue from the growth inhibitory effect of p53 by ING1 antisense RNA (i.e., GSE) expression was confirmed in co-transfection experiments. 10(1) cells were transfected using the calcium phosphate method (see Ossovskaya et al., 1996, Proc. Natl. Acad Sci. USA 93: 10309–10314) with a plasmid encoding wild type p53 and either a vector encoding the anti-ING1 GSE, the anti-p53 GSE termed GSE56 ((see Ossovskaya et al., ibid.) or the vector alone and selected in 200 µg/mL hygromycin. The results of these experiments are shown in FIG. 4B. Expression of p53 with the anti-ING1 GSE results in no observed growth suppression. Similarly, growth suppression was not observed in cells co-transfected by p53 and GSE56. In the cells expressing the p53 plasmid (and the endogenous mouse p33$^{ING1}$), growth suppression was observed.

These results indicated that both p53 and ING1 must be co-expressed in mammalian cells to confer the growth suppression phenotype on the cells, and suggested that p53 and p33$^{ING1}$ act cooperatively in mediating the growth suppression phenotype.

EXAMPLE 4 p33$^{ING1}$ is a Mediator of Transcriptional Activation by p53

In view of the results obtained in Examples 2 and 3 above, mammalian cells were assayed to determine the role of p33$^{ING1}$ in transcriptional activation of p53-responsive genes. The growth inhibitory effect of p53 was known to be mediated by transcriptional activation of a p53-responsive inhibitor of cyclin-dependent kinases, p21$^{WAF1}$ (see El-Deiry el al., 1993, Cell 75: 817–825). To analyze the effect of ING1 expression on this important function of p53, a series of experiments were performed using a reporter expression construct in which the bacterial gene for chloramphenicol acetyltransferase (CAT) was under the control of a combination of a p53-responsive binding site from the WAF1 gene promoter with the minimal heat shock Hsp70 (see Kondratov et al., 1996, Molecular Biology (Russia) 30: 613–620).

These cells were prepared as follows. $2 \times 10^5$ cells per 60-mm dish were transfected with a total of 12 µg of plasmid DNA containing 4 µg of pWAF1-CAT and 2 gg of pCMV-lacZ. Cell extracts were prepared by freezing and thawing and were normalized for protein content. The efficiency of transfection was determined by using a quantitative β-galactosidase assay.

Two different cell lines expressing the wild typep53 gene (human HT1080 and rat REF52), and the p53-deficicnt Balb/c 3T3 cell line 10(1) described above, were transfected with the reporter plasmid in combination with plasmids expressing either ING1 cDNA (encoding p28$^{ING1}$), anti-ING1 GSE, a dominant negative p53 mutant genetic suppressor element (GSE56), or with control insert-free plasmid. For experiments performed using the p53-deficient 10(1) cells, plasmid expressing wild type p53 cDNA was also added. Extracts from the transfected cells were prepared and CAT assays performed using conventional techniques (see Sambrook el al., ibid.).

Figure 5:
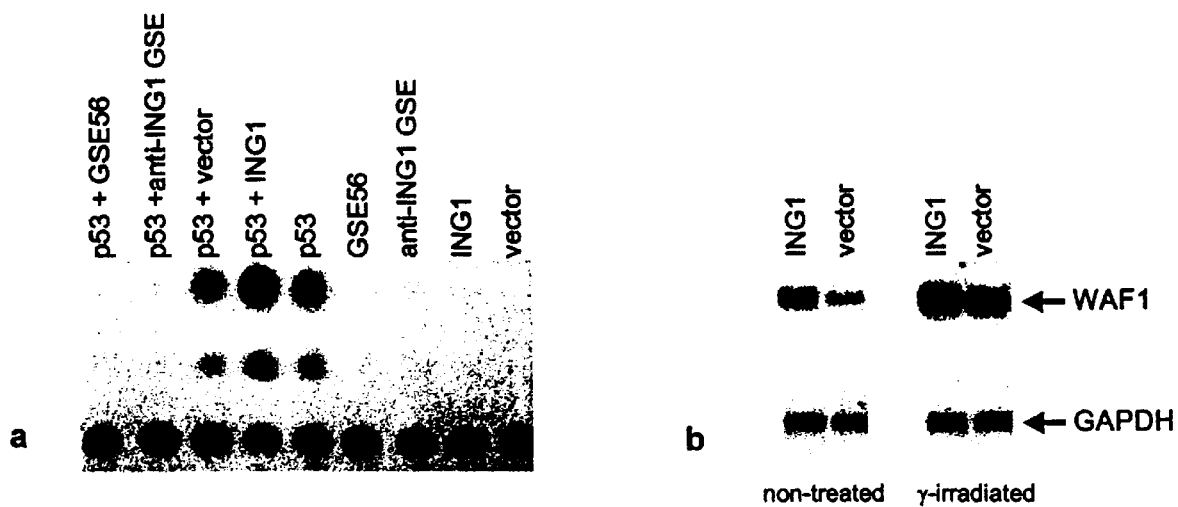
FIG. 5A illustrates the results of CAT assays carried out with the extracts of 10(1) cells co-transfected with a combination of pWAF1-CAT plasmid and the indicated constructs.
FIG. 5B shows Northern blot hybridization with WAF1-specific probe; GAPDH-specific probe was used as loading control. WAF1 mRNA expression is increased in normal and γ-irradiated HT 1080 cells overexpressing ING1.

The results of one of these experiments are shown in FIG. 5A. 10(1) cells transfected with and expressing p53+GSE56, p53+anti-ING1 GSE, GSE56, anti-ING1 GSE, ING1 or the vector alone showed no detectable CAT activity, consistent with the absence of p53 activity in these cells. CAT activity was detected in cells expressing p53, either alone (p53 or p53+vector) or co-expressed with exogenously-added human p28$^{ING1}$ (p53+ING1). p53-dependent CAT activity in transfected cells was stimulated 2–4-fold in the presence of the ING1-expressing construct (p53+ING1) and significantly inhibited (3–5 fold) by ING1 antisense GSE. The inhibitory effect of the anti-ING1 GSE was comparable to that of anti-p53 GSE56. Similar results were obtained with the other cell lines tested. These results indicated that the function of p53 as a transcriptional activator depends on the presence of p28$^{ING1}$, and suggested that the growth inhibition activity associated with ING1 gene expression involves stimulation of p53 transcriptional activity.

Expression of the endogenous WAF1 gene is also affected by ING1 expression. HT1080 cells overexpressing ING1 cDNA (resulting from transfection with the p28$^{ING1}$-encoding plasmid disclosed above) contain 4–6 times more WAF1 mRNA than control cells. These results are shown in FIG. 5B. RNA was isolated from HT1080 cells transfected with the p28 IGI-encoding plasmid or vector alone and assayed by Northern blot hybridization (Sambrook et al., ibid.) probed with a radiolabeled WAF1 cDNA probe; a radiolabeled GAPDH probe was included in the hybridization as a loading control. In the autoradiograms shown in FIG. 5B, the amount of WAF1 mRNA on the Northern blot is greater in the lanes containing RNA isolated from cells transfected with the $p28^{ING1}$-encoding plasmid than in the lanes containing RNA isolated from cells transfected with the plasmid vector alone. This difference is retained even in gamma-irradiated HT1080 cells that induce WAF1 expression by a p53-dependent mechanism.

These results demonstrated that ING1 expression is required for the transcriptional activation mediated by p53, and that overexpression of ING1 gene product increases the degree of transcriptional activation in cells expressing p53.

EXAMPLE 5

Physical Interaction of $p33^{ING1}$ and p53 Proteins

The close association of the biochemical activities of p53 and $p33^{ING1}$ suggested that these proteins are capable of physically interaction,for example, by forming a complex between the two types of molecules. In order to determine whether the functional interdependence of p53 and $p33^{ING1}$ was accompanied by physical interaction between the molecules, co-immunoprecipitation experiments were performed as follows. Cells growing in 100-mm tissue culture dishes (containing approximately $3 \times 10^6$ cells per dish) were washed with ice-cold phosphate buffered saline (PBS), scraped into 1 mL of RIPA buffer (see Harlow & Lane, 1988, *Antibodies: A Laboratory Manual*, Cold Spring Harbor Laboratory Press: New York, p. 447) not containing detergents such as SDS, and sonicated. The extracts were cleared by centrifugation at 10,000 g for 10 min. A mixture of PAb421 and DO-1 monoclonal antibodies were added to cell extract and incubated for 2 hours at 4° C. 30 μL of protein A Sepharose equilibrated in RIPA were then added and incubated for additional 30 min. The beads were extensively washed with ice-cold RIPA and the precipitate was dissolved in a sample buffer for electrophoresis and Western blot analysis. Western blotting was performed, using the anti-GST-$p33^{ING1}$ rabbit polyclonal antibodies against a bacterially expressed gluthatione-S-transferase-$p33^{ING1}$ fused protein (prepared as disclosed in International Application, Publication No. WO97/21809, incorporated by reference) or a mixture of anti-p53 monoclonal antibodies produced by hybridomas PAb421 and DO1 (provided by Arnold Levine). Biotinylated donkey anti-rabbit or sheep anti-mouse antibodies were used by secondary ones. Antibody binding was visualized by enhanced chemiluminescence using horseradish peroxidase conjugated with streptavidin (Amersham).

Figure 6:
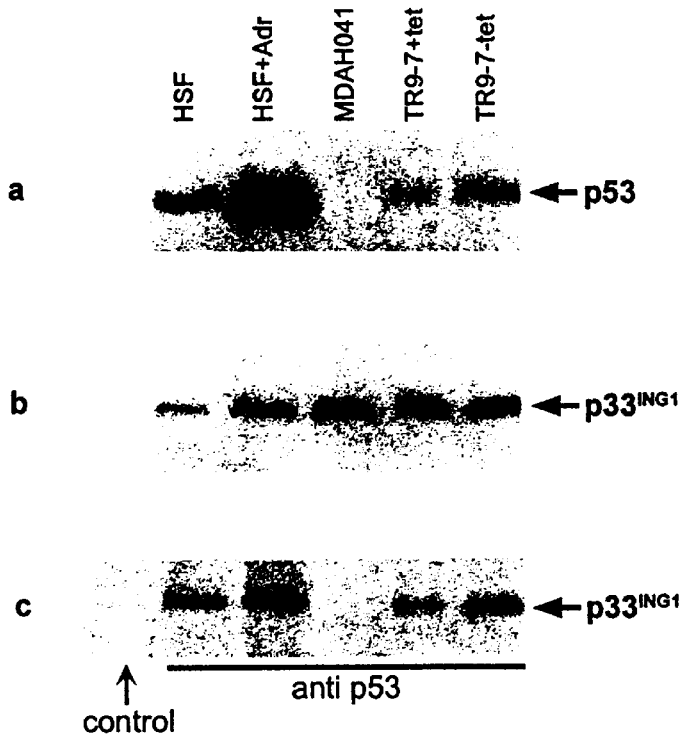
FIGS. 6A through 6C shows the results of Western blotting of immunoprecipitation of p53 with anti-p53 antibody (FIG. 6A); immunoprecipitation of $p33^{ING1}$ with anti-$p33^{ING1}$ polyclonal antibody (FIG. 6B) and $p33^{ING1}$ detected on Western blots immunoprecipitation of p53 with anti-p53 antibody (FIG. 6C).

In these experiments, anti-p53 antibodies (PAb421 and DO1) were used to precipitate p53-containing protein complexes from cellular extracts. The presence of $p33^{ING1}$ protein in these precipitates was monitored by immunoblotting with polyclonal antibodies against $p33^{ING1}$. Several cell types, differing in p53 expression levels, were assayed, including: wild type human skin fibroblasts (HSF), growing under normal conditions or treated with the chemotherapeutic drug Adriamycin to induce p53 stabilization; human fibroblasts from a patient with Li-Fraumeni syndrome (line MDAH041),which lack expression of p53; and a derivatives of MDAH041 carrying a tetracycline-regulated wild type p53 cDNA (TR9–7; see Agarwal et al., 1995, *Proc. Natl. Acad. Sci. USA* 92: 8493–8497); in TR9-7 cells maintained in the presence of 1 μg/mL of tetracycline, p53 expression is suppressed, which p53 expression is induced by incubation without tetracycline for 24 hours. All these cells expressed similar levels of $p33^{ING1}$, as shown in FIG. 6B, indicating that $p33^{ING1}$ expression was not affected by p53 expression or drug-induced DNA damage. $p33^{ING1}$ protein was detected in anti-p53 antibody precipitates in all the cells expressing wild type p53 (HSF, HSF + Adriamycin, and TR9-7 cells; FIG. 6B), and the amount of $p33^{ING1}$ in precipitates correlated with the p53 content (compare FIG. 6A and FIG. 6B). In contrast, no $p33^{ING1}$ protein was found in anti-p53 antibody precipitates from the extracts of p53-null MDAH041 cells (FIG. 6C), consistent with the lack of p53 expression in these cells. In similar experiments, a polyclonal antisera against $p33^{ING1}$ co-precipitated a 53 KDa protein from an extract of $^{35}$S-methionine labeled cells expressing wild type p53 but not from the p53-null cells, thus confirming physical association between p53 and $p33^{ING1}$.

Taken together, the results disclosed in Examples 2 through 5 herein demonstrated that $p33^{ING1}/p28^{ING1}$ (collectively termed "ING1 gene expression") directly cooperates with p53 in growth regulation by modulating the ability of p53 to act as a transcriptional activator. Reduction of ING1 gene expression was found to inhibit the growth suppressive activity of p53, suggesting that $p33^{ING1}$ is essential for p53 function. The mechanism of $p33^{ING1}$/p53 cooperation involves physical interaction between these two proteins, which form a complex detectable by immunoprecipitation. These data places ING1 into a family of p53-interacting proteins, such as mdm2, Rb-1 and p300, which modulate p53 activity through physical interaction (see Momand et al., 1992, *Cell* 69: 1237–1245; Jayaraman et al., 1997, *Genes Devel.* 11: 558–570; Avantaggiati el al., 1997, *Cell* 89: 1175–1184). The involvement of ING1 gene expression in the p53 signaling pathway points to ING1 as a new tumor suppressor gene whose loss or inactivation may contribute to altered cell growth, resistance to apoptosis, or establishment of the immortal phenotype in tumors retaining wild type p53.

EXAMPLE 6

Diagnostic Assay

The existence of the ING1 tumor suppressor gene suggests that the phenotype of altered cell growth, resistance to apoptosis, or establishment of the immortal phenotype in tumors or premalignant cells, which has heretofore been associated with alterations in expression of p53, may occur even in cells in which the p53 gene continues to be expressed. Thus, the recognition that inhibition of ING1 expression is associated with certain types of clinical malignancy and with cellular growth control suggests that diagnostic assays determining ING1 gene expression levels are useful for assessing patient disease status or risk for developing malignant disease.

Diagnostics assays provided by the invention involve determining gene expression levels of $p33^{ING1}/p28^{ING1}$ in cell or tissue samples from an individual. In the practice of such assays, mRNA levels are determined using conventional assays including reverse transcription—polymerase chain reaction (RT-PCR; Kawasaki & Wang, *ibid.*), preferably quantitative embodiments thereof (see Noonan el al., 1990, *Proc. Natl. Acad. Sci. USA* 87: 7160–7164), by standard filter hybridization procedures (including Northern blot hybridization), or by RNase protection assay. In these assays, RNA is extracted from cells or tissue samples from a human to be tested, and the aforesaid assays performed, most preferably in parallel with similar assays either from normal cells or tissue of the individual, or with a panel of standardized cell lines expressing known amounts of p33$^{ING1}$/p28$^{ING1}$. Comparison of the ING1 gene expression levels in the cell or tissue sample from the human with ING1 gene expression levels in the normal cell or tissue sample from the human or the panel of standardized cell lines is used to determine whether ING1 gene expression is reduced or absent in the cell or tissue sample. A determination of reduced or absent ING1 gene expression is associated with malignancy or premalignancy in the individual, or with an increased risk of developing a malignant disease.

Alternatively, p33$^{ING1}$/p28$^{ING1}$ production in a cell or tissue sample from an individual is determined directly using antibodies produced against the ING1 gene product. Conventional immunoassays are used, preferably quantitative immunoassay (e.g., RIA or immunohistochemical assays) to determine the amount of the ING1 gene product that is present in the a sample. In the practice of this embodiment of the methods of the invention, immunoassay is performed on proteins extracted from the cell or tissue sample to be tested. Alternatively, immunostaining assays are used to detect p33$^{ING1}$/p28$^{ING1}$ expression in the cells or tissues tested. Polyclonal or monoclonal antibodies are useful in the diagnostic assays of the invention. Comparison of p33$^{ING1}$/p28$^{ING1}$ expression in the cell or tissue sample with expression in normal cells or tissue from the individual, or with a standardized panel of cell lines is preformed to determine whether the tested cell or tissue sample has reduced or absent p33$^{ING1}$/p28$^{ING1}$ expression levels.

It should be understood that the foregoing disclosure emphasizes certain specific embodiments of the invention and that all modifications or alternatives equivalent thereto are within the spirit and scope of the invention as set forth in the appended claims.

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 182 base pairs
      (B) TYPE: nucleic acid
      (C) STRANDEDNESS: single
      (D) TOPOLOGY: linear (ii) MOLECULE TYPE: cDNA (iv) ANTI-SENSE: YES (xi) SEQUENCE DESCRIPTION: SEQ ID NO:1:

```
TTGTAGTTTC TAAAATGCTG ATCCACAGAC CACTTTCTTG TTACACGTGT ACCAATGAAA      60

ACAAAAGGCA AACAGAATCA CTGCCATCCC TATGAAAGGA ATGGTTCCTT TTCTAACATT     120

CTTTAAAAAT ATACATTTTA CACTCCTTGC ACCTCAACAA AGGCAGCAAT GTAATAAATA     180

CA                                                                    182
```

(2) INFORMATION FOR SEQ ID NO:2:

(i) SEQUENCE CHARACTERISTICS:
      (A) LENGTH: 2061 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 16..897

(xi) SEQUENCE DESCRIPTION: SEQ ID NO:2:

```
GAGTAACCCG ATAAT ATG CCG TTG TGC ACG GCG ACG AGA ATT CCC AGA TAT      51
               Met Pro Leu Cys Thr Ala Thr Arg Ile Pro Arg Tyr
                 1               5                  10

AGC AGT AGC AGT GAT CCC GGG CCT GTG GCT CGG GGC CGG GGC TGC AGT       99
Ser Ser Ser Ser Asp Pro Gly Pro Val Ala Arg Gly Arg Gly Cys Ser
         15                  20                  25
```

```
                              -continued

TCG GAC CGC CTC CCG CGA CCC GCG GGG CCG GCT CGG AGA CAG TTT CAG      147
Ser Asp Arg Leu Pro Arg Pro Ala Gly Pro Ala Arg Arg Gln Phe Gln
    30                  35                  40

GCC GCA TCT TTG CTG ACC CGA GGG TGG GGC CGC GCG TGG CCG TGG AAA      195
Ala Ala Ser Leu Leu Thr Arg Gly Trp Gly Arg Ala Trp Pro Trp Lys
45                  50                  55                  60

CAG ATC CTG AAG GCG CTA GAC GAG TGC TAC GAG CGC TTC AGT CGC GAG      243
Gln Ile Leu Lys Ala Leu Asp Glu Cys Tyr Glu Arg Phe Ser Arg Glu
                65                  70                  75

ACA GAC GGG GCG CAG AAG CGG CGG ATG CTG CAC TGT GTG CAG CGC GCG      291
Thr Asp Gly Ala Gln Lys Arg Arg Met Leu His Cys Val Gln Arg Ala
            80                  85                  90

CTG ATC CGC AGC CAG GAG CTG GGC GAC GAG AAG ATC CAG ATC GTG AGC      339
Leu Ile Arg Ser Gln Glu Leu Gly Asp Glu Lys Ile Gln Ile Val Ser
        95                  100                 105

CAG ATG GTG GAG CTG GTG GAG AAC CGC ACG CGG CAG GTG GAC AGC CAC      387
Gln Met Val Glu Leu Val Glu Asn Arg Thr Arg Gln Val Asp Ser His
    110                 115                 120

GTG GAG CTG TTC GAG GCG CAG CAG GAG CTG GGC GAC ACA GTG GGC AAC      435
Val Glu Leu Phe Glu Ala Gln Gln Glu Leu Gly Asp Thr Val Gly Asn
125                 130                 135                 140

AGC GGC AAG GTT GGC GCG GAC AGG CCC AAT GGC GAT GCG GTA GCG CAG      483
Ser Gly Lys Val Gly Ala Asp Arg Pro Asn Gly Asp Ala Val Ala Gln
                145                 150                 155

TCT GAC AAG CCC AAC AGC AAG CGC TCA CGG CGG CAG CGC AAC AAC GAG      531
Ser Asp Lys Pro Asn Ser Lys Arg Ser Arg Arg Gln Arg Asn Asn Glu
            160                 165                 170

AAC CGT GAG AAC GCG TCC AGC AAC CAC GAC CAC GAC GAC GGC GCC TCG      579
Asn Arg Glu Asn Ala Ser Ser Asn His Asp His Asp Asp Gly Ala Ser
        175                 180                 185

GGC ACA CCC AAG GAG AAG AAG GCC AAG ACC TCC AAG AAG AAG AAG CGC      627
Gly Thr Pro Lys Glu Lys Lys Ala Lys Thr Ser Lys Lys Lys Lys Arg
    190                 195                 200

TCC AAG GCC AAG GCG GAG CGA GAG GCG TCC CCT GCC GAC CTC CCC ATC      675
Ser Lys Ala Lys Ala Glu Arg Glu Ala Ser Pro Ala Asp Leu Pro Ile
205                 210                 215                 220

GAC CCC AAC GAA CCC ACG TAC TGT CTG TGC AAC CAG GTC TCC TAT GGG      723
Asp Pro Asn Glu Pro Thr Tyr Cys Leu Cys Asn Gln Val Ser Tyr Gly
                225                 230                 235

GAG ATG ATC GGC TGC GAC AAC GAC GAG TGC CCC ATC GAG TGG TTC CAC      771
Glu Met Ile Gly Cys Asp Asn Asp Glu Cys Pro Ile Glu Trp Phe His
            240                 245                 250

TTC TCG TGC GTG GGG CTC AAT CAT AAA CCC AAG GGC AAG TGG TAC TGT      819
Phe Ser Cys Val Gly Leu Asn His Lys Pro Lys Gly Lys Trp Tyr Cys
        255                 260                 265

CCC AAG TGC CGG GGG GAG AAC GAG AAG ACC ATG GAC AAA GCC CTG GAG      867
Pro Lys Cys Arg Gly Glu Asn Glu Lys Thr Met Asp Lys Ala Leu Glu
    270                 275                 280

AAA TCC AAA AAA GAG AGG GCT TAC AAC AGG TAGTTTGTGG ACAGGCGCCT        917
Lys Ser Lys Lys Glu Arg Ala Tyr Asn Arg
285                 290

GGTGTGAGGA GGACAAAATA AACCGTGTAT TTATTACATT GCTGCCTTTG TTGAGGTGCA    977

AGGAGTGTAA AATGTATATT TTTAAAGAAT GTTAGAAAAG GAACCATTCC TTTCATAGGG   1037

ATGGCAGTGA TTCTGTTTGC CTTTTGTTTT CATTGGTACA CGTGTAACAA GAAAGTGGTC   1097

TGTGGATCAG CATTTTAGAA ACTACAAATA TAGGTTTGAT TCAACACTTA AGTCTCAGAC   1157

TGATTTCTTG CGGGAGGAGG GGGACTAAAC TCACCCTAAC ACATTAAATG TGGAAGGAAA   1217

ATATTTCATT AGCTTTTTTA TTTTAATACA AGTAATATTA TTACTTTATG AACAATTTTT   1277
```

```
TTTAATTGGC CATGTCGCCA AAAATACAGC CTATAGTAAA TGTGTTTCTT GCTGCCATGA    1337

TGTATATCCA TATAACAATT CAGTAACAAA GGTTTAAAGT TTGAAGATTA TTTTTTAAAA    1397

AGGTAAAAGG TTAAATTTTA CATGACAGAT ATTTTATCTA TTGGCCTGTT CCCCAAATGG    1457

CCATTTTAAA ATGCTTGGGT ACACTTCTCT TAAGTGGTCT AGTCAAGGAA CCTCAAGTCA    1517

TGCTTTTGCT ATCACCAATC ATAGTGTACC CATCTTTAAT TTATATCAGG TGTATAAATG    1577

TACATTTCCA AATGAACTTG CACTGTAATA TTATAATTGG AAGTGCAGTC AGCAGTAGCT    1637

GTCGGAGCTA ATGTCACAAT TATGTGCAAA GGTGTGCTTC CTGCTGTATG TGAGCTGTAA    1697

AAATGTTACG TGAAGAAATA AATGAAACTT GGCCAGTTTG TTCCTCTAGT AGTATATTTA    1757

ATTTTGACAT AAGTAACTTT TAAAATTTGT CTTAAAAATT TATACACCAG CAATTTAGAC    1817

AAAGCCTTAA GCAAATTTTG TATTATTGTT CTCACTTATT ATTAATAATG AAGTAGAAGT    1877

TACTTAATTG CCAGCAAATA AATACGTGTC AAAAAGAAT CTGTATTCAG ACCCCTGGGG    1937

TCAGGAAATT ACTGCCCCAC TTGTCAAGTT CAGCCCACCA TCTGTTTGAA CATTATATGA    1997

AGTTTAAATT CTAGTGTCCA TAAATAAAGT TTCAGCGGCA CCCCAAAAAA AAAAAAAAA    2057

AAAA    2061
```

(2) INFORMATION FOR SEQ ID NO:3:

(i) SEQUENCE CHARACTERISTICS:
        (A) LENGTH: 294 amino acids
        (B) TYPE: amino acid
        (D) TOPOLOGY: linear (ii) MOLECULE TYPE: protein (xi) SEQUENCE DESCRIPTION: SEQ ID NO:3:

```
Met Pro Leu Cys Thr Ala Thr Arg Ile Pro Arg Tyr Ser Ser Ser
  1               5                  10                  15

Asp Pro Gly Pro Val Ala Arg Gly Arg Gly Cys Ser Ser Asp Arg Leu
                 20                  25                  30

Pro Arg Pro Ala Gly Pro Ala Arg Arg Gln Phe Gln Ala Ala Ser Leu
             35                  40                  45

Leu Thr Arg Gly Trp Gly Arg Ala Trp Pro Trp Lys Gln Ile Leu Lys
 50                  55                  60

Ala Leu Asp Glu Cys Tyr Glu Arg Phe Ser Arg Glu Thr Asp Gly Ala
 65                  70                  75                  80

Gln Lys Arg Arg Met Leu His Cys Val Gln Arg Ala Leu Ile Arg Ser
                 85                  90                  95

Gln Glu Leu Gly Asp Glu Lys Ile Gln Ile Val Ser Gln Met Val Glu
            100                 105                 110

Leu Val Glu Asn Arg Thr Arg Gln Val Asp Ser His Val Glu Leu Phe
            115                 120                 125

Glu Ala Gln Gln Glu Leu Gly Asp Thr Val Gly Asn Ser Gly Lys Val
130                 135                 140

Gly Ala Asp Arg Pro Asn Gly Asp Ala Val Ala Gln Ser Asp Lys Pro
145                 150                 155                 160

Asn Ser Lys Arg Ser Arg Arg Gln Arg Asn Asn Glu Asn Arg Glu Asn
                165                 170                 175

Ala Ser Ser Asn His Asp His Asp Asp Gly Ala Ser Gly Thr Pro Lys
            180                 185                 190

Glu Lys Lys Ala Lys Thr Ser Lys Lys Lys Arg Ser Lys Ala Lys
            195                 200                 205
```

```
       Ala Glu Arg Glu Ala Ser Pro Ala Asp Leu Pro Ile Asp Pro Asn Glu
           210                 215                 220

Pro Thr Tyr Cys Leu Cys Asn Gln Val Ser Tyr Gly Glu Met Ile Gly
       225                 230                 235                 240

Cys Asp Asn Asp Glu Cys Pro Ile Glu Trp Phe His Phe Ser Cys Val
                       245                 250                 255

Gly Leu Asn His Lys Pro Lys Gly Lys Trp Tyr Cys Pro Lys Cys Arg
                       260                 265                 270

Gly Glu Asn Glu Lys Thr Met Asp Lys Ala Leu Glu Lys Ser Lys Lys
                   275                 280                 285

Glu Arg Ala Tyr Asn Arg
           290

(2) INFORMATION FOR SEQ ID NO:4:

(i) SEQUENCE CHARACTERISTICS:
         (A) LENGTH: 873 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: CDS
         (B) LOCATION: 7..813

(xi) SEQUENCE DESCRIPTION: SEQ ID NO:4:

TGAACC ATG TTG AGT CCT GCC AAC GGG GAG CAG CTC CAC CTG GTG AAC         48
       Met Leu Ser Pro Ala Asn Gly Glu Gln Leu His Leu Val Asn
         1               5                  10

TAT GTG GAG GAC TAC CTG GAC TCC ATC GAG TCC CTG CCT TTC GAC TTG         96
Tyr Val Glu Asp Tyr Leu Asp Ser Ile Glu Ser Leu Pro Phe Asp Leu
 15                  20                  25                  30

CAG AGA AAT GTC TCG CTG ATG CGG GAG ATC GAC GCG AAA TAC CAA GAG        144
Gln Arg Asn Val Ser Leu Met Arg Glu Ile Asp Ala Lys Tyr Gln Glu
                 35                  40                  45

ATC CTG AAG GAG CTA GAC GAG TGC TAC GAG CGC TTC AGT CGC GAG ACA        192
Ile Leu Lys Glu Leu Asp Glu Cys Tyr Glu Arg Phe Ser Arg Glu Thr
         50                  55                  60

GAC GGG GCG CAG AAG CGG CGG ATG CTG CAC TGT GTG CAG CGC GCG CTG        240
Asp Gly Ala Gln Lys Arg Arg Met Leu His Cys Val Gln Arg Ala Leu
             65                  70                  75

ATC CGC AGC CAG GAG CTG GGC GAC GAG AAG ATC CAG ATC GTG AGC CAG        288
Ile Arg Ser Gln Glu Leu Gly Asp Glu Lys Ile Gln Ile Val Ser Gln
 80                  85                  90

ATG GTG GAG CTG GTG GAG AAC CGC ACG CGG CAG GTG GAC AGC CAC GTG        336
Met Val Glu Leu Val Glu Asn Arg Thr Arg Gln Val Asp Ser His Val
 95                 100                 105                 110

GAG CTG TTC GAG GCG CAG CAG GAG CTG GGC GAC ACA GTG GGC AAC AGC        384
Glu Leu Phe Glu Ala Gln Gln Glu Leu Gly Asp Thr Val Gly Asn Ser
                115                 120                 125

GGC AAG GTT GGC GCG GAC AGG CCC AAT GGC GAT GCG GTA GCG CAG TCT        432
Gly Lys Val Gly Ala Asp Arg Pro Asn Gly Asp Ala Val Ala Gln Ser
            130                 135                 140

GAC AAG CCC AAC AGC AAG CGC TCA CGG CGG CAG CGC AAC AAC GAG AAC        480
Asp Lys Pro Asn Ser Lys Arg Ser Arg Arg Gln Arg Asn Asn Glu Asn
        145                 150                 155

CGT GAG AAC GCG TCC AGC AAC CAC GAC CAC GAC GAC GGC GCC TCG GGC        528
Arg Glu Asn Ala Ser Ser Asn His Asp His Asp Asp Gly Ala Ser Gly
    160                 165                 170
```

```
ACA CCC AAG GAG AAG AAG GCC AAG ACC TCC AAG AAG AAG AAG CGC TCC      576
Thr Pro Lys Glu Lys Lys Ala Lys Thr Ser Lys Lys Lys Arg Ser
175             180                 185                 190

AAG GCC AAG GCG GAG CGA GAG GCG TCC CCT GCC GAC CTC CCC ATC GAC      624
Lys Ala Lys Ala Glu Arg Glu Ala Ser Pro Ala Asp Leu Pro Ile Asp
                195                 200                 205

CCC AAC GAA CCC ACG TAC TGT CTG TGC AAC CAG GTC TCC TAT GGG GAG      672
Pro Asn Glu Pro Thr Tyr Cys Leu Cys Asn Gln Val Ser Tyr Gly Glu
        210                 215                 220

ATG ATC GGC TGC GAC AAC GAC GAG TGC CCC ATC GAG TGG TTC CAC TTC      720
Met Ile Gly Cys Asp Asn Asp Glu Cys Pro Ile Glu Trp Phe His Phe
            225                 230                 235

TCG TGC GTG GGG CTC AAT CAT AAA CCC AAG GGC AAG TGG TAC TGT CCC      768
Ser Cys Val Gly Leu Asn His Lys Pro Lys Gly Lys Trp Tyr Cys Pro
240                 245                 250

AAG TGC CGG GGG GAG AAC GAG AAG ACC ATG GAC AAA GCC CTG GAG          813
Lys Cys Arg Gly Glu Asn Glu Lys Thr Met Asp Lys Ala Leu Glu
255                 260                 265

AAATCCAAAA AAGAGAGGGC TTACAACAGG TAGTTTGTGG ACAGGCGCCT GGTGTGAGGA    873
```

(2) INFORMATION FOR SEQ ID NO:5:

(i) SEQUENCE CHARACTERISTICS:
        (A) LENGTH: 269 amino acids
        (B) TYPE: amino acid
        (D) TOPOLOGY: linear (ii) MOLECULE TYPE: protein (xi) SEQUENCE DESCRIPTION: SEQ ID NO:5:

```
Met Leu Ser Pro Ala Asn Gly Glu Gln Leu His Leu Val Asn Tyr Val
1               5                   10                  15

Glu Asp Tyr Leu Asp Ser Ile Glu Ser Leu Pro Phe Asp Leu Gln Arg
            20                  25                  30

Asn Val Ser Leu Met Arg Glu Ile Asp Ala Lys Tyr Gln Glu Ile Leu
        35                  40                  45

Lys Glu Leu Asp Glu Cys Tyr Glu Arg Phe Ser Arg Glu Thr Asp Gly
    50                  55                  60

Ala Gln Lys Arg Arg Met Leu His Cys Val Gln Arg Ala Leu Ile Arg
65                  70                  75                  80

Ser Gln Glu Leu Gly Asp Glu Lys Ile Gln Ile Val Ser Gln Met Val
                85                  90                  95

Glu Leu Val Glu Asn Arg Thr Arg Gln Val Asp Ser His Val Glu Leu
            100                 105                 110

Phe Glu Ala Gln Gln Glu Leu Gly Asp Thr Val Gly Asn Ser Gly Lys
        115                 120                 125

Val Gly Ala Asp Arg Pro Asn Gly Asp Ala Val Ala Gln Ser Asp Lys
    130                 135                 140

Pro Asn Ser Lys Arg Ser Arg Arg Gln Arg Asn Asn Glu Asn Arg Glu
145                 150                 155                 160

Asn Ala Ser Ser Asn His Asp His Asp Asp Gly Ala Ser Gly Thr Pro
                165                 170                 175

Lys Glu Lys Lys Ala Lys Thr Ser Lys Lys Lys Arg Ser Lys Ala
            180                 185                 190

Lys Ala Glu Arg Glu Ala Ser Pro Ala Asp Leu Pro Ile Asp Pro Asn
        195                 200                 205

Glu Pro Thr Tyr Cys Leu Cys Asn Gln Val Ser Tyr Gly Glu Met Ile
```

```
              210                 215                 220
Gly Cys Asp Asn Asp Glu Cys Pro Ile Glu Trp Phe His Phe Ser Cys
225                 230                 235                 240

Val Gly Leu Asn His Lys Pro Lys Gly Lys Trp Tyr Cys Pro Lys Cys
                245                 250                 255

Arg Gly Glu Asn Glu Lys Thr Met Asp Lys Ala Leu Glu
                260                 265

(2) INFORMATION FOR SEQ ID NO:6:

(i) SEQUENCE CHARACTERISTICS:
        (A) LENGTH: 633 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..630

(xi) SEQUENCE DESCRIPTION: SEQ ID NO:6:

ATG CTG CAC TGT GTG CAG CGC GCG CTG ATC CGC AGC CAG GAG CTG GGC      48
Met Leu His Cys Val Gln Arg Ala Leu Ile Arg Ser Gln Glu Leu Gly
 1               5                  10                  15

GAC GAG AAG ATC CAG ATC GTG AGC CAG ATG GTG GAG CTG GTG GAG AAC      96
Asp Glu Lys Ile Gln Ile Val Ser Gln Met Val Glu Leu Val Glu Asn
                20                  25                  30

CGC ACG CGG CAG GTG GAC AGC CAC GTG GAG CTG TTC GAG GCG CAG CAG     144
Arg Thr Arg Gln Val Asp Ser His Val Glu Leu Phe Glu Ala Gln Gln
         35                  40                  45

GAG CTG GGC GAC ACA GTG GGC AAC AGC GGC AAG GTT GGC GCG GAC AGG     192
Glu Leu Gly Asp Thr Val Gly Asn Ser Gly Lys Val Gly Ala Asp Arg
 50                  55                  60

CCC AAT GGC GAT GCG GTA GCG CAG TCT GAC AAG CCC AAC AGC AAG CGC     240
Pro Asn Gly Asp Ala Val Ala Gln Ser Asp Lys Pro Asn Ser Lys Arg
 65                  70                  75                  80

TCA CGG CGG CAG CGC AAC AAC GAG AAC CGT GAG AAC GCG TCC AGC AAC     288
Ser Arg Arg Gln Arg Asn Asn Glu Asn Arg Glu Asn Ala Ser Ser Asn
                85                  90                  95

CAC GAC CAC GAC GAC GGC GCC TCG GGC ACA CCC AAG GAG AAG AAG GCC     336
His Asp His Asp Asp Gly Ala Ser Gly Thr Pro Lys Glu Lys Lys Ala
                100                 105                 110

AAG ACC TCC AAG AAG AAG AAG CGC TCC AAG GCC AAG GCG GAG CGA GAG     384
Lys Thr Ser Lys Lys Lys Lys Arg Ser Lys Ala Lys Ala Glu Arg Glu
        115                 120                 125

GCG TCC CCT GCC GAC CTC CCC ATC GAC CCC AAC GAA CCC ACG TAC TGT     432
Ala Ser Pro Ala Asp Leu Pro Ile Asp Pro Asn Glu Pro Thr Tyr Cys
130                 135                 140

CTG TGC AAC CAG GTC TCC TAT GGG GAG ATG ATC GGC TGC GAC AAC GAC     480
Leu Cys Asn Gln Val Ser Tyr Gly Glu Met Ile Gly Cys Asp Asn Asp
145                 150                 155                 160

GAG TGC CCC ATC GAG TGG TTC CAC TTC TCG TGC GTG GGG CTC AAT CAT     528
Glu Cys Pro Ile Glu Trp Phe His Phe Ser Cys Val Gly Leu Asn His
                165                 170                 175

AAA CCC AAG GGC AAG TGG TAC TGT CCC AAG TGC CGG GGG GAG AAC GAG     576
Lys Pro Lys Gly Lys Trp Tyr Cys Pro Lys Cys Arg Gly Glu Asn Glu
                180                 185                 190

AAG ACC ATG GAC AAA GCC CTG GAG AAA TCC AAA AAA GAG AGG GCT TAC     624
Lys Thr Met Asp Lys Ala Leu Glu Lys Ser Lys Lys Glu Arg Ala Tyr
        195                 200                 205
```

```
AAC AGG TAG                                                    633
Asn Arg
    210

(2) INFORMATION FOR SEQ ID NO:7:

(i) SEQUENCE CHARACTERISTICS:
        (A) LENGTH: 210 amino acids
        (B) TYPE: amino acid
        (D) TOPOLOGY: linear (ii) MOLECULE TYPE: protein (xi) SEQUENCE DESCRIPTION: SEQ ID NO:7:

Met Leu His Cys Val Gln Arg Ala Leu Ile Arg Ser Gln Glu Leu Gly
 1               5                  10                  15

Asp Glu Lys Ile Gln Ile Val Ser Gln Met Val Glu Leu Val Glu Asn
                20                  25                  30

Arg Thr Arg Gln Val Asp Ser His Val Glu Leu Phe Glu Ala Gln Gln
            35                  40                  45

Glu Leu Gly Asp Thr Val Gly Asn Ser Gly Lys Val Gly Ala Asp Arg
 50                  55                  60

Pro Asn Gly Asp Ala Val Ala Gln Ser Asp Lys Pro Asn Ser Lys Arg
 65                  70                  75                  80

Ser Arg Arg Gln Arg Asn Asn Glu Asn Arg Glu Asn Ala Ser Ser Asn
                85                  90                  95

His Asp His Asp Asp Gly Ala Ser Gly Thr Pro Lys Glu Lys Lys Ala
                100                 105                 110

Lys Thr Ser Lys Lys Lys Arg Ser Lys Ala Lys Ala Glu Arg Glu
            115                 120                 125

Ala Ser Pro Ala Asp Leu Pro Ile Asp Pro Asn Glu Pro Thr Tyr Cys
    130                 135                 140

Leu Cys Asn Gln Val Ser Tyr Gly Glu Met Ile Gly Cys Asp Asn Asp
145                 150                 155                 160

Glu Cys Pro Ile Glu Trp Phe His Phe Ser Cys Val Gly Leu Asn His
                165                 170                 175

Lys Pro Lys Gly Lys Trp Tyr Cys Pro Lys Cys Arg Gly Glu Asn Glu
            180                 185                 190

Lys Thr Met Asp Lys Ala Leu Glu Lys Ser Lys Lys Glu Arg Ala Tyr
        195                 200                 205

Asn Arg
    210
```

We claim:

1. An isolated nucleic acid encoding an amino acid sequence of a mammalian ING1 gene product identified by SEQ ID No. 5.

2. A recombinant expression construct comprising a nucleic acid according to claim 1.

3. A eukaryotic cell transformed with the recombinant expression construct of claim 2.

* * * * *